(12) United States Patent
Collier et al.

(10) Patent No.: US 9,713,668 B2
(45) Date of Patent: Jul. 25, 2017

(54) MULTI-STAGED FILTRATION SYSTEM FOR BLOOD FLUID REMOVAL

(71) Applicants: Kenneth J Collier, Dellwood, MN (US); Bryant J Pudil, Plymouth, MN (US); Martin T Gerber, Maple Grove, MN (US)

(72) Inventors: Kenneth J Collier, Dellwood, MN (US); Bryant J Pudil, Plymouth, MN (US); Martin T Gerber, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 415 days.

(21) Appl. No.: 14/369,602

(22) PCT Filed: Jan. 4, 2013

(86) PCT No.: PCT/US2013/020404
§ 371 (c)(1),
(2) Date: Oct. 15, 2014

(87) PCT Pub. No.: WO2013/103906
PCT Pub. Date: Jul. 11, 2013

(65) Prior Publication Data
US 2015/0258268 A1 Sep. 17, 2015

Related U.S. Application Data

(60) Provisional application No. 61/583,001, filed on Jan. 4, 2012.

(51) Int. Cl.
*A61M 1/34* (2006.01)
*B01D 63/00* (2006.01)
(Continued)

(52) U.S. Cl.
CPC .......... *A61M 1/3472* (2013.01); *A61M 1/14* (2013.01); *A61M 1/16* (2013.01); *A61M 1/1633* (2014.02);
(Continued)

(58) Field of Classification Search
CPC ........ A61M 1/14; A61M 1/16; A61M 1/1633; A61M 1/34; A61M 1/3472; A61M 1/3475;
(Continued)

(56) References Cited

U.S. PATENT DOCUMENTS 3,608,729 A 9/1971 Haselden
3,669,878 A 6/1972 Marantz
(Continued)

FOREIGN PATENT DOCUMENTS

CN 101883594 A 11/2010
EP 0264695 A2 * 10/1987
(Continued)

OTHER PUBLICATIONS

PCT/US2013/020404, International Search Report, Jan. 4, 2013.
(Continued)

*Primary Examiner* — John Kim
(74) *Attorney, Agent, or Firm* — Roger Hahn

(57) ABSTRACT

A device includes (i) a housing defining an interior, wherein the interior has a blood compartment, a plasma compartment, and a fluid compartment; (ii) a first filter disposed in the interior of the housing, and (iii) a second filter disposed in the interior of the housing. The first filter separates at least a portion of the blood compartment from at least a portion of the plasma compartment. The first filter is configured to allow plasma components, but not cell components, of blood to pass through the first filter from the blood compartment to the plasma compartment. The second filter separates at least
(Continued)

a portion of the plasma compartment from at least a portion of the fluid compartment. The second filter is configured to allow fluid and small molecules, but not larger components, to pass through the second filter from the plasma compartment to the fluid compartment. The device may include a sorbent in the plasma compartment to remove or reduce the concentration of selected components of the plasma. In embodiments, a system including the device includes a sorbent with which the plasma may be contacted.

23 Claims, 14 Drawing Sheets

(51) Int. Cl.
| | | |
|---|---|---|
| B01D 61/14 | (2006.01) | |
| A61M 1/16 | (2006.01) | |
| B01D 15/08 | (2006.01) | |
| A61M 1/14 | (2006.01) | |
| B01D 61/28 | (2006.01) | |
| B01D 63/04 | (2006.01) | |
| B01D 63/08 | (2006.01) | |
| B01D 61/24 | (2006.01) | |

(52) U.S. Cl.
CPC ............ *A61M 1/34* (2013.01); *A61M 1/3475* (2014.02); *B01D 15/08* (2013.01); *B01D 61/145* (2013.01); *B01D 61/28* (2013.01); *B01D 63/00* (2013.01); *B01D 63/043* (2013.01); *B01D 63/08* (2013.01); *A61M 1/3479* (2014.02); *A61M 1/3482* (2014.02); *A61M 1/3486* (2014.02); *A61M 2205/75* (2013.01); *B01D 61/243* (2013.01); *B01D 2313/40* (2013.01); *B01D 2317/02* (2013.01); *B01D 2319/06* (2013.01)

(58) Field of Classification Search
CPC .............. A61M 1/3479; A61M 1/3482; A61M 1/3486; A61M 2205/75; B01D 15/08; B01D 2313/40; B01D 2317/02; B01D 2319/06; B01D 61/145; B01D 61/243; B01D 61/28; B01D 63/00; B01D 63/043; B01D 63/08
See application file for complete search history.

(56) References Cited

U.S. PATENT DOCUMENTS

| | | | |
|---|---|---|---|
| 3,669,880 A | 6/1972 | Marantz | |
| 3,776,819 A | 12/1973 | Williams | |
| 3,850,835 A | 11/1974 | Marantz | |
| 3,884,808 A | 5/1975 | Scott | |
| 3,902,490 A | 9/1975 | Jacobsen et al. | |
| 3,989,622 A | 11/1976 | Marantz | |
| 4,060,485 A | 11/1977 | Eaton | |
| 4,209,392 A | 6/1980 | Wallace | |
| 4,371,385 A | 2/1983 | Johnson | |
| 4,374,382 A | 2/1983 | Markowitz | |
| 4,376,707 A | 3/1983 | Lehmann | |
| 4,381,999 A | 5/1983 | Boucher | |
| 4,460,555 A | 7/1984 | Thompson | |
| 4,556,063 A | 12/1985 | Thompson | |
| 4,562,751 A | 1/1986 | Nason | |
| 4,581,141 A | 4/1986 | Ash | |
| 4,650,587 A | 3/1987 | Polak | |
| 4,678,408 A | 7/1987 | Mason | |
| 4,685,903 A | 8/1987 | Cable | |
| 4,750,494 A | 6/1988 | King | |
| 4,816,162 A | 3/1989 | Rosskopf et al. | |
| 4,826,663 A | 5/1989 | Alberti | |
| 4,828,693 A | 5/1989 | Lindsay | |
| 5,015,388 A * | 5/1991 | Pusineri | A61M 1/3472 210/314 |
| 5,080,653 A | 1/1992 | Voss | |
| 5,092,886 A | 3/1992 | Dobos-Hardy | |
| 5,097,122 A | 3/1992 | Colman | |
| 5,127,404 A | 7/1992 | Wyborny | |
| 5,230,702 A | 7/1993 | Lindsay et al. | |
| 5,284,470 A | 2/1994 | Beltz | |
| 5,302,288 A | 4/1994 | Meidl | |
| 5,305,745 A | 4/1994 | Zacouto | |
| 5,308,315 A | 5/1994 | Khuri | |
| 5,318,750 A | 6/1994 | Lascombes | |
| 5,468,388 A | 11/1995 | Goddard | |
| 5,507,723 A | 4/1996 | Keshaviah | |
| 5,662,806 A | 9/1997 | Keshaviah et al. | |
| 5,683,432 A | 11/1997 | Goedeke | |
| 5,762,782 A | 6/1998 | Kenley | |
| 5,849,179 A | 12/1998 | Emerson et al. | |
| 5,858,186 A | 1/1999 | Glass | |
| 5,944,684 A | 8/1999 | Roberts | |
| 6,048,732 A | 4/2000 | Anslyn | |
| 6,052,622 A | 4/2000 | Holmstrom | |
| 6,058,331 A | 5/2000 | King | |
| 6,114,176 A | 9/2000 | Edgson et al. | |
| 6,126,831 A | 10/2000 | Goldau et al. | |
| 6,230,059 B1 | 5/2001 | Duffin | |
| 6,248,093 B1 | 6/2001 | Moberg | |
| 6,254,567 B1 | 7/2001 | Treu | |
| 6,321,101 B1 | 11/2001 | Holmstrom | |
| 6,362,591 B1 | 3/2002 | Moberg | |
| 6,363,279 B1 | 3/2002 | Ben-Haim | |
| 6,521,184 B1 | 2/2003 | Edgson et al. | |
| 6,554,798 B1 | 4/2003 | Mann | |
| 6,555,986 B2 | 4/2003 | Moberg | |
| 6,589,229 B1 | 7/2003 | Connelly | |
| 6,602,399 B1 | 8/2003 | Fromherz | |
| 6,627,164 B1 | 9/2003 | Wong | |
| 6,666,840 B1 | 12/2003 | Falkvall et al. | |
| 6,676,608 B1 | 1/2004 | Keren | |
| 6,711,439 B1 | 3/2004 | Bradley | |
| 6,719,745 B1 | 4/2004 | Taylor | |
| 6,814,724 B2 | 11/2004 | Taylor | |
| 6,818,196 B2 | 11/2004 | Wong | |
| 6,861,266 B1 | 3/2005 | Sternby | |
| 6,878,283 B2 | 4/2005 | Thompson | |
| 6,960,179 B2 | 11/2005 | Gura | |
| 7,033,498 B2 | 4/2006 | Wong | |
| 7,077,819 B1 | 7/2006 | Goldau | |
| 7,101,519 B2 | 9/2006 | Wong | |
| 7,208,092 B2 | 4/2007 | Micheli | |
| 7,241,272 B2 | 7/2007 | Karoor et al. | |
| 7,276,042 B2 | 10/2007 | Polaschegg et al. | |
| 7,326,576 B2 | 2/2008 | Womble et al. | |
| 7,435,342 B2 | 10/2008 | Tsukamoto | |
| 7,488,447 B2 | 2/2009 | Sternby | |
| 7,537,688 B2 | 5/2009 | Tarumi et al. | |
| 7,544,300 B2 | 6/2009 | Brugger et al. | |
| 7,544,737 B2 | 6/2009 | Poss et al. | |
| 7,563,240 B2 | 7/2009 | Gross et al. | |
| 7,566,432 B2 | 7/2009 | Wong | |
| 7,575,564 B2 | 8/2009 | Childers | |
| 7,597,806 B2 | 10/2009 | Uchi et al. | |
| 7,674,231 B2 | 3/2010 | McCombie | |
| 7,704,361 B2 | 4/2010 | Garde | |
| 7,736,507 B2 | 6/2010 | Wong | |
| 7,754,852 B2 | 7/2010 | Burnett | |
| 7,756,572 B1 | 7/2010 | Fard | |
| 7,776,210 B2 | 8/2010 | Rosenbaum | |
| 7,794,141 B2 | 9/2010 | Perry | |
| 7,794,419 B2 | 9/2010 | Paolini et al. | |
| 7,850,635 B2 | 12/2010 | Polaschegg et al. | |
| 7,867,214 B2 | 1/2011 | Childers | |
| 7,922,686 B2 | 4/2011 | Childers et al. | |
| 7,922,911 B2 | 4/2011 | Micheli | |
| 7,947,179 B2 | 5/2011 | Rosenbaum | |
| 7,955,290 B2 | 6/2011 | Karoor et al. | |
| 7,967,022 B2 | 6/2011 | Grant | |
| 7,981,082 B2 | 7/2011 | Wang | |
| 7,988,854 B2 | 8/2011 | Tsukamoto | |

(56) References Cited

U.S. PATENT DOCUMENTS

| | | |
|---|---|---|
| 8,002,726 B2 | 8/2011 | Karoor et al. |
| 8,029,454 B2 | 10/2011 | Kelly et al. |
| 8,034,161 B2 | 10/2011 | Gura |
| 8,066,658 B2 | 11/2011 | Karoor et al. |
| 8,070,709 B2 | 12/2011 | Childers |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo et al. |
| 8,183,046 B2 | 5/2012 | Lu |
| 8,187,250 B2 | 5/2012 | Roberts et al. |
| 8,197,439 B2 | 6/2012 | Wang et al. |
| 8,246,826 B2 | 8/2012 | Wilt |
| 8,273,049 B2 | 9/2012 | Demers |
| 8,292,594 B2 | 10/2012 | Tracey |
| 8,303,532 B2 | 11/2012 | Hamada et al. |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,404,091 B2 | 3/2013 | Ding et al. |
| 8,409,441 B2 | 4/2013 | Wilt |
| 8,409,444 B2 | 4/2013 | Wong |
| 8,499,780 B2 | 8/2013 | Wilt |
| 8,518,260 B2 | 8/2013 | Raimann |
| 8,535,525 B2 | 9/2013 | Heyes |
| 8,580,112 B2 | 11/2013 | Updyke |
| 8,597,227 B2 | 12/2013 | Childers |
| 8,696,626 B2 | 4/2014 | Kirsch |
| 8,777,892 B2 | 7/2014 | Sandford |
| 8,903,492 B2 | 12/2014 | Soykan |
| 8,906,240 B2 | 12/2014 | Crnkovich |
| 9,144,640 B2 | 9/2015 | Pudil |
| 2002/0042561 A1 | 4/2002 | Schulman |
| 2002/0112609 A1 | 8/2002 | Wong |
| 2003/0080059 A1 | 5/2003 | Peterson et al. |
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers et al. |
| 2004/0099593 A1 | 5/2004 | DePaolis |
| 2004/0102732 A1 | 5/2004 | Naghavi et al. |
| 2004/0147900 A1 | 7/2004 | Polaschegg |
| 2004/0215090 A1 | 10/2004 | Erkkila |
| 2005/0006296 A1 | 1/2005 | Sullivan |
| 2005/0065760 A1 | 3/2005 | Murtfeldt |
| 2005/0113796 A1 | 5/2005 | Taylor |
| 2005/0126961 A1 | 6/2005 | Bissler |
| 2005/0126998 A1 | 6/2005 | Childers |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0195064 A1 | 8/2006 | Plahey |
| 2006/0217771 A1 | 9/2006 | Soykan |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger et al. |
| 2007/0066928 A1 | 3/2007 | Lannoy |
| 2007/0138011 A1 | 6/2007 | Hofmann |
| 2007/0175827 A1 | 8/2007 | Wariar |
| 2007/0179431 A1 | 8/2007 | Roberts et al. |
| 2007/0213665 A1 | 9/2007 | Curtin et al. |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0051696 A1 | 2/2008 | Curtin |
| 2008/0053905 A9 | 3/2008 | Brugger et al. |
| 2008/0067132 A1 | 3/2008 | Ross |
| 2008/0215247 A1 | 9/2008 | Tonelli |
| 2009/0020471 A1 | 1/2009 | Tsukamoto |
| 2009/0101577 A1 | 4/2009 | Fulkerson |
| 2009/0127193 A1 | 5/2009 | Updyke |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2010/0004588 A1 | 1/2010 | Yeh et al. |
| 2010/0007838 A1 | 1/2010 | Fujimoto |
| 2010/0010429 A1 | 1/2010 | Childers |
| 2010/0078381 A1 | 4/2010 | Merchant |
| 2010/0078387 A1 | 4/2010 | Wong |
| 2010/0084330 A1 | 4/2010 | Wong |
| 2010/0094158 A1 | 4/2010 | Solem |
| 2010/0100027 A1 | 4/2010 | Schilthuizen et al. |
| 2010/0102190 A1 | 4/2010 | Zhu et al. |
| 2010/0114012 A1 | 5/2010 | Sandford |
| 2010/0137693 A1 | 6/2010 | Porras |
| 2010/0168546 A1 | 7/2010 | Kamath |
| 2010/0217181 A1 | 8/2010 | Roberts et al. |
| 2010/0224492 A1 | 9/2010 | Ding et al. |
| 2010/0234795 A1 | 9/2010 | Wallenas |
| 2010/0241045 A1 | 9/2010 | Kelly |
| 2010/0282662 A1* | 11/2010 | Lee ............... A61M 1/3472 210/266 |
| 2011/0017665 A1 | 1/2011 | Updyke |
| 2011/0048949 A1 | 3/2011 | Ding et al. |
| 2011/0066043 A1 | 3/2011 | Banet |
| 2011/0077574 A1 | 3/2011 | Sigg |
| 2011/0079558 A1 | 4/2011 | Raimann |
| 2011/0087187 A1 | 4/2011 | Beck |
| 2011/0120930 A1 | 5/2011 | Mishkin |
| 2011/0130666 A1 | 6/2011 | Dong |
| 2011/0163034 A1 | 7/2011 | Castellarnau |
| 2011/0184340 A1 | 7/2011 | Tan |
| 2011/0272337 A1 | 11/2011 | Palmer |
| 2011/0297593 A1 | 12/2011 | Kelly |
| 2012/0016228 A1 | 1/2012 | Kroh |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0248017 A1 | 10/2012 | Beiriger |
| 2012/0258546 A1 | 10/2012 | Marran |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2013/0037465 A1 | 2/2013 | Heyes |
| 2013/0199998 A1 | 8/2013 | Kelly |
| 2013/0213890 A1 | 8/2013 | Kelly |
| 2013/0274642 A1 | 10/2013 | Soykan |
| 2013/0324915 A1 | 12/2013 | Britton |
| 2013/0330208 A1 | 12/2013 | Ly |
| 2013/0331774 A1 | 12/2013 | Farrell |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0217028 A1 | 8/2014 | Pudil |
| 2014/0217030 A1 | 8/2014 | Meyer |
| 2014/0220699 A1 | 8/2014 | Pudil |
| 2014/0251908 A1 | 9/2014 | Ding |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0258268 A1 | 9/2015 | Collier |
| 2015/0352270 A1 | 12/2015 | Pudil |

(56) References Cited

U.S. PATENT DOCUMENTS

FOREIGN PATENT DOCUMENTS

| | | |
|---|---|---|
| EP | 266795 A2 | 11/1987 |
| EP | 711182 B1 | 6/2003 |
| EP | 1364666 A1 | 11/2003 |
| EP | 0906768 B1 | 2/2004 |
| EP | 1450879 | 10/2008 |
| EP | 1592494 B1 | 6/2009 |
| EP | 2100553 A1 | 9/2009 |
| EP | 2575827 A2 | 12/2010 |
| EP | 2100553 | 8/2011 |
| EP | 2576453 A2 | 12/2011 |
| EP | 2701580 | 11/2012 |
| EP | 2701595 | 11/2012 |
| EP | 1545652 B1 | 1/2013 |
| EP | 1345856 B1 | 3/2013 |
| EP | 2344220 B1 | 4/2013 |
| EP | 2701596 | 3/2014 |
| JP | 5099464 | 10/2012 |
| WO | 9532010 A1 | 11/1995 |
| WO | 9937342 | 7/1999 |
| WO | 0057935 | 10/2000 |
| WO | 0066197 A1 | 11/2000 |
| WO | 0170307 A1 | 9/2001 |
| WO | 0185295 A2 | 9/2001 |
| WO | 0185295 A2 | 11/2001 |
| WO | 03043677 A2 | 5/2003 |
| WO | 03043680 | 5/2003 |
| WO | 03051422 A2 | 6/2003 |
| WO | 2004008826 | 1/2004 |
| WO | 2004009156 | 1/2004 |
| WO | 2004030716 A2 | 4/2004 |
| WO | 2004030717 A2 | 4/2004 |
| WO | 2004064616 A2 | 8/2004 |
| WO | 2004062710 A3 | 10/2004 |
| WO | 2005123230 A2 | 12/2005 |
| WO | 2006124431 A2 | 11/2006 |
| WO | 2007089855 A2 | 8/2007 |
| WO | 2009026603 | 12/2008 |
| WO | 2009026603 A1 | 3/2009 |
| WO | 2009067071 A1 | 5/2009 |
| WO | 2009157877 A1 | 12/2009 |
| WO | 2009157878 A1 | 12/2009 |
| WO | 2010028860 A1 | 2/2010 |
| WO | 2010028860 | 3/2010 |
| WO | 2010102190 A4 | 11/2010 |
| WO | 2011025705 A1 | 3/2011 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013028809 A3 | 2/2013 |
| WO | 2013019994 A3 | 4/2013 |
| WO | 2013025844 A3 | 5/2013 |
| WO | 2013103607 A1 | 7/2013 |
| WO | 2013103906 | 7/2013 |
| WO | 2013114063 A1 | 8/2013 |
| WO | 2013121162 A1 | 8/2013 |
| WO | 14066254 | 5/2014 |
| WO | 2014066255 | 5/2014 |
| WO | 2014077082 | 5/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

PCT/US2014/014357 International Search Report and Written Opinion, (May 2014).
Weissman, S., et al., "Hydroxyurea-induced hepatitis in human immunodeficiency virus-positive patients." Clin. Infec. Dis, (Jul. 29, 1999): 223-224.
Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
MacLean, et, al., Effects of hindlimb contraction on pressor and muscle interstitial metabolite responses in the cat, J. App. Physiol., 1998, 1583-1592, 85 (4).
Overgaard, et. al., Activity-induced recovery of excitability in K+-depressed rat soieus muscle, Am. J. P• Regulatory Integrative Comp Physiol, 280: R48-R55 (2001).
Overgaard. et. al., Relations between excitability and contractility in rate soleus'muscle: role of the NA+-K+ pump and NA+-K-S gradients. Journal of Physiology, 1999, 215-225, 518(1).
Roberts M, The regenerative dialysis (REDY) sorbent system. Nephrology, 1998, 275-278:4.
Ronco et al. 2008, 'Cardiorenal Syndrome,' Journal American College Cardiology, 52:1527-1539, Abstract.
Siegenthalar, et al., Pulmonary fluid status monitoring with intrathoracic impedance, Journal of Clinical Monitoring and Computing, 24:449-451, 2010.
U.S. Appl. No. 13/424,479.
Wang, Fundamentals of intrathoracic impedance monitoring in heart failure, Am. J. Cardiology, 2007, 3G-10G: Suppl.
PCT/US2014/067650 International Search Report Written Opinion mailed Mar. 9, 2015.
Brynda, et. al., The detection of toman 2-microglcbuiin by grating coupler immunosensor with three dimensional antibody networks. Biosensors & Bioelectronics, 1999, 363-368, 14(4).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, Aug. 13, 2013.
PCT/US2012/034331, International Search Report, Jul. 9, 2012.
PCT/US2012/034332, International Search Report, Jul. 5, 2012.
PCT/US2012/034334, International Search Report, Jul. 6, 2012.
PCT/US2012/034335, International Search Report, Sep. 5, 2012.
Redfield, et. al, Restoration of renal response to atrial natriuretic factor in experimental low-output heat failure, Am. J. Physiol., 1989, R917-923:257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Leifer et al., 'A Study on the Temperature Variation of Rise Velocity for Large Clean Bubbles,' J. Atmospheric & Oceanic Tech., vol. 17, pp. 1392-1402, (Oct. 2000).
Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Talaia, 'Terminal Velocity of a Bubble Rise in a Liquid Column,' World Acad. of Sci., Engineering & Tech., vol. 28, pp. 264-268 (2007).
The FHN Trial Group. In-Center. Hemodialysis Six Times per Week versus Three Times per Week, New England Journal of Medicine, 2010 Abstract.
Coast, et al. 1990, An approach to Cardiac Arrhythmia analysis Using Hidden Markov Models, IEEE Transactions on Biomedical Engineering. 1990, 37 (9):826-835.
PCT/US2012/034330, International Preliminary Report on Patentability, Oct. 29, 2013.

(56) References Cited

OTHER PUBLICATIONS

PCT/US2012/034333, International Preliminary Report on Patentability, Oct. 29, 2013.
PCT/US2012/034333, International Search Report, Aug. 29, 2013.
Bleyer, et. al., Sudden and cardiac death rated in hemodialysis patients, Kidney International. 1999, 1553-1559: 55.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Gambro AK 96 Dialysis Machine Operator's Manual, Dec. 2012.

* cited by examiner

US 9,713,668 B2

MULTI-STAGED FILTRATION SYSTEM FOR BLOOD FLUID REMOVAL

FIELD OF THE INVENTION

The present disclosure relates generally to devices, systems and methods for hemodialysis, ultrafiltration, and the like.

BACKGROUND

Blood fluid removal processes, such as hemodialysis and ultrafiltration, typically employ a filter or membrane across which fluid, and some waste products, may be removed from blood. The blood, with reduced fluid or waste products, is then returned to the patient.

SUMMARY OF THE INVENTION

This disclosure, among other things, describes devices, systems and methods that include pre-filtering blood to separate plasma from cellular components of blood and subjecting the plasma to at least one additional fluid removal process. Pre-filtering reduces or eliminates cells and clotting factors that contact the filter used to remove fluid from the plasma, thereby reducing the likelihood of fouling secondary filtering systems, which may increase longevity of such secondary filtering systems or components thereof. The devices, systems and processes described herein may allow for lower concentrations of anticoagulants to be used in the blood fluid removal process, and thus may reduce the amount of anticoagulants present in blood returned to the patient.

In embodiments described herein, a method includes separating a patient's blood into a plasma component and a cell component. Fluid is then removed from the plasma component to obtain a reduced-fluid plasma. The fluid may be removed by dialysis, ultrafiltration, or the like. The reduced-fluid plasma may be combined with the cell component and may be returned to the patient. In embodiments, at least some of the reduced-fluid plasma is recirculated for additional fluid removal or treatment through the dialysis process, the ultrafiltration process, or the like. The plasma or reduced fluid plasma may be contacted with a sorbent to remove or reduce the concentration of one or more additional components of the plasma or reduced-fluid plasma.

In embodiments described herein, a device includes (i) a housing defining an interior, wherein the interior has a blood compartment, a plasma compartment, and a fluid compartment; (ii) a first filter disposed in the interior of the housing, and (iii) a second filter disposed in the interior of the housing. The first filter separates at least a portion of the blood compartment from at least a portion of the plasma compartment. The first filter is configured to allow plasma components, but not cell components, of blood to pass through the first filter from the blood compartment to the plasma compartment. The second filter separates at least a portion of the plasma compartment from at least a portion of the fluid compartment. The second filter is configured to allow fluid and small molecules, but not larger components, to pass through the second filter from the plasma compartment to the fluid compartment. The device may include a sorbent in either the plasma or reduced-fluid compartment to remove or reduce the concentration of selected components of the plasma. In embodiments, a system including the device includes a sorbent with which the plasma or reduced-fluid plasma may be contacted.

One or more embodiments of the systems, devices and methods described herein may provide one or more advantages over prior systems, devices and methods for blood fluid removal in patients. For example, the processes described herein may result in reduced likelihood of fouling of membranes, and thus may allow for use of lowered concentrations of anticoagulant. By pre-filtering blood cells and other large components, such as clotting factors, the efficiency of the blood fluid removal process may be increased and may allow for a reduction in the size of the fluid removal filter employed. Pre-filtering blood cells and other large components may allow more ready use of sorbents for selective removal of components from plasma, where the presence of cells and clotting factors may result in fouling, and inefficient use, of the sorbent. These and other advantages will be apparent to those of skilled in the art upon reading the following detailed description.

In one or more embodiments of the systems, devices and methods described herein, one or more efficiencies may be obtained by having additional filtration systems or sorbent systems for use in the same compartments.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
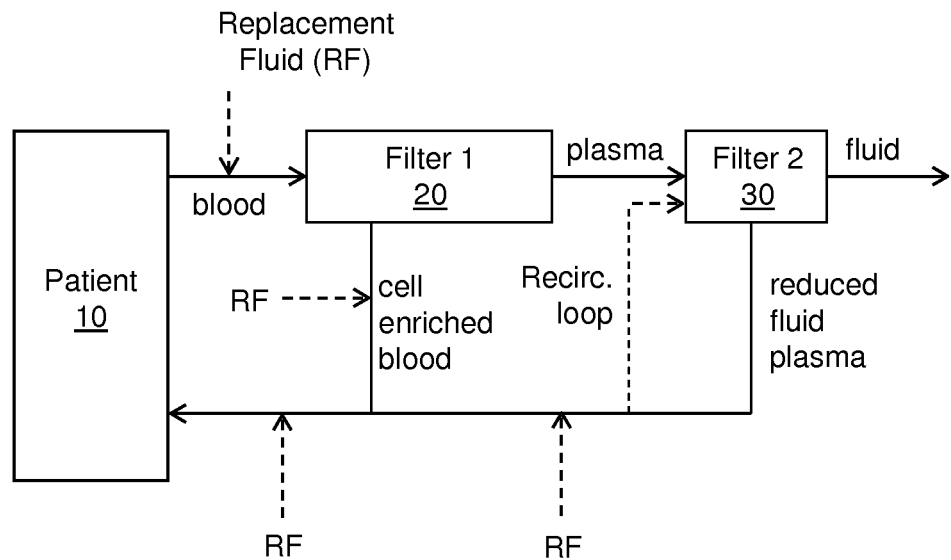
FIGS. 1-3 are schematic block diagrams showing interaction of components of embodiments of blood fluid removal devices or systems with a patient illustrating flow of blood and fluid.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION OF THE INVENTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Consisting essentially of", as it relates to a device, system, or method, means that the device, system, or method includes only the recited components or steps of the device, system, or method and, optionally, other components or steps that do not materially affect the basic and novel properties of the device, system, or methods.

"Consisting of" and "consisting essentially of" are subsumed within "comprising." For example, a filter comprising a porous membrane may be a filter consisting essentially of, or consisting of, the porous membrane.

Any direction referred to herein, such as "top," "bottom," "left," "right," "upper," "lower," "above," below," and other directions and orientations are described herein for clarity in reference to the figures and are not to be limiting of an actual device or system or use of the device or system. Many of the devices or systems described herein may be used in a number of directions and orientations.

As used herein, a "blood fluid removal process," or the like, refers to a process from which fluid is removed from blood, or one or more components thereof, such as plasma. Often the blood, or component thereof, is returned to a patient after the fluid is removed. In many cases, the blood, or component thereof, is also cleaned; i.e., waste products are removed from the blood, or component thereof, and cleaned blood, or component thereof, is returned to the patient. Examples of blood fluid removal processes include ultrafiltration, hemofiltration, hemodialysis, hemodiafiltration, peritoneal dialysis and the like. It will be understood that, during some of these processes, fluid may be introduced to blood, or components thereof, before it is returned to the patient, and thus the returned blood, or components thereof, may not have a reduced fluid volume even though it has been subjected to a blood fluid removal process. Any patient for which a blood fluid removal process is indicated may benefit from the devices, systems and methods described herein.

As used herein, a "patient for which a blood fluid removal process is indicated" is a patient that has undergone, is undergoing, or is likely to undergo at least one blood fluid removal process wherein the blood is further processed and returned to the patient. In general, such patients are fluid overloaded patients, such as patients suffering from heart failure, chronic kidney disease, or acute kidney failure. Often such patients are stage 3 to stage 5 chronic kidney disease patients, are often unresponsive or under-responsive to diuretics, or the like.

As used herein, "plasma," "plasma component of blood," or the like, refer to a liquid component of blood in which some or all cells or other large components, such as components greater than about 0.2 microns (e.g., greater than about 0.5 microns or greater than about 1 micron), have been removed. In embodiments, cells or other large components are removed by filtration; e.g., by passing across a filter having a molecular weight cutoff of about 500,000 Da.

As used herein, "reduced-fluid plasma" refers to plasma from which at least some fluid has been removed or which has been subjected to a blood fluid removal process.

As used herein, "cell-enriched blood" means blood from which at least some fluid, such as plasma, has been removed so that the concentration of cells in the remaining blood is enriched relative to the blood prior to fluid removal.

As used herein, "filtered blood" means blood that has been subjected to a blood fluid removal process or blood that has been recombined with components of blood, such as plasma, that have been subjected to a blood fluid removal process.

As used herein, a "cell component" of blood is a component of blood that retains cells when plasma has been removed the blood. The cell component of blood may include plasma. For example, the cell component may retain some plasma when the blood has been separated into a cell component and a plasma component.

As used herein, "filtering fluid" means subjecting the fluid, such as plasma or blood, to a blood fluid removal process.

As used herein, "dialyzed plasma" means plasma that has been subjected to a dialysis procedure, such as hemodialysis, hemodiafiltration, or the like.

As used herein, "dialyzed blood" means blood that has been subjected to a dialysis procedure or blood that contains components, such as plasma, that have been subjected to a dialysis procedure. For example, blood that contains dialyzed plasma is dialyzed blood for the purposes of this disclosure.

As used herein, a "porous fiber" is a membrane having a body forming a lumen, wherein the body contains pores within a size range that allow for passage of some solutes across the membrane through the pores but which restrict passage of other solutes across the membrane. The pores may be a series of interconnected voids formed in the body. In some embodiments, the membrane is configured to allow passage of plasma through the pores, but to restrict passage of cellular components of blood.

As used herein, a "sorbent" is a substance that has the property to collect molecules of another substance by sorption; e.g., by adsorption or absorption. A sorbent medium is a sorbent through, or around, which a substance, such as blood or plasma, may be passed so that molecules from the substance may be sorbed to the sorbent medium.

As used herein, in the context of a blood fluid removal device, system, or components thereof, "blood compartment" is an enclosed space in which blood or cell-enriched blood is contained. Typically, at least a portion of the blood compartment is defined by a first filter configured to selectively allow plasma, but not cellular components of blood, to pass.

As used herein, in the context of a blood fluid removal device, system, or components thereof, "plasma compartment" is an enclosed space in which plasma that has been separated from blood is contained. Typically, at least a portion of the plasma compartment is defined by a first filter that selectively allows plasma, but not cellular components of blood, to pass. At least a portion of the plasma compartment may be defined by second filter configured to allow smaller molecules (such as molecules less than about 60,000 Da), but not larger molecules (such as molecules greater than about 60,000 Da), to pass.

As used herein, a "first filter" that separates a blood compartment from a plasma compartment is a membrane, which may be a porous fiber, configured to allow selective passage of plasma, but not cellular components of blood, across the membrane.

As used herein, a "second filter" that separates a plasma compartment from a fluid compartment is a membrane, which may be a porous fiber, configured to allow selective passage of small molecules, but not larger molecules, across the membrane. In embodiments, the membrane is configured to allow selective passage of molecules of less than about 60,000 Da, but generally not molecules larger than about 60,000 Da.

This disclosure, among other things, relates to devices, systems and methods that pre-filter blood to separate plasma from larger components, including cells. The plasma may then be subjected to a fluid removal process. By subjecting plasma, rather than blood, to a fluid removal process, the likelihood of fouling the blood fluid removal filter is reduced, which may increase the efficiency of fluid removal, may allow for a reduction in overall filter size, or may allow for reduced concentrations of anticoagulants to be used. Further, the separated plasma may be more amenable to sorbent treatment than blood, which may tend to clot and foul sorbents configured to selectively remove components from blood.

Any suitable device or system for removing fluid, or fluid and contaminants, from blood may be used in accordance with the teachings presented herein. The devices, or components thereof, may be traditional large console-type, wearable, or implantable.

Figure 2:
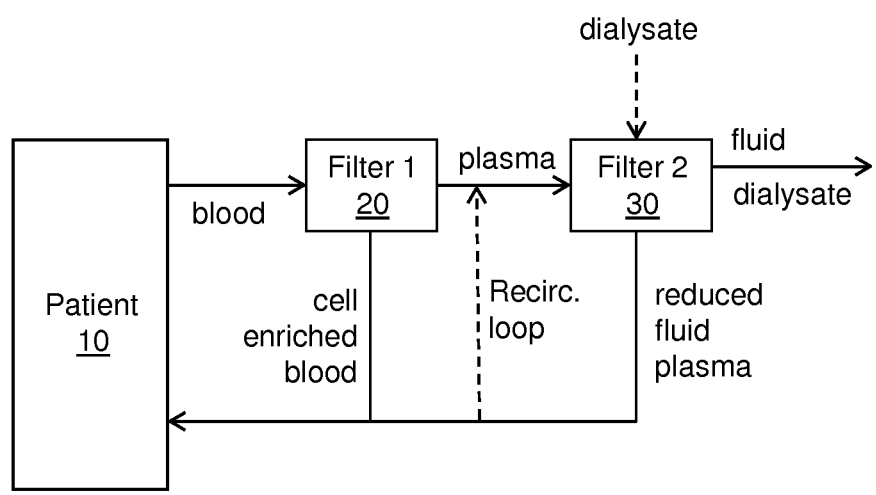
Figure 3:
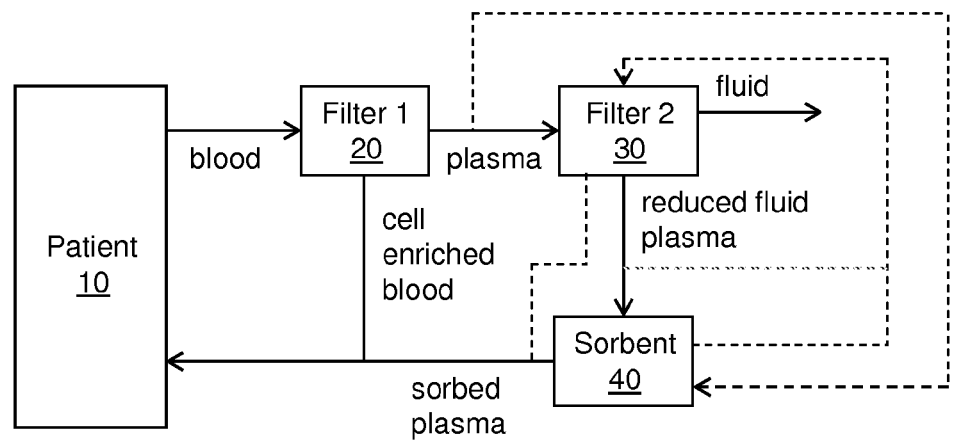

Block diagrams of some components of blood fluid devices or systems are shown in FIGS. 1-3. As shown in, e.g., FIG. 1 blood may be removed from a patient 10 and may be filtered via a first filter 20 to separate the blood into plasma and cell enriched blood. As used herein, "cell enriched blood" means blood from which some fluid or plasma component has been removed. During most processes described herein, the cell enriched blood will retain some fluid or plasma component and will remain flowable in the device or system.

The first filter 20 may be any filter configured to allow plasma to pass through the filter and to block cells or other large components from blood from passing through the filter. In embodiments, the first filter 20 has a pore size between about 0.1 microns and about 0.65 microns. Such filters preferably restrict or exclude passage of cells and other large components of blood, such as clotting factors. Such filters are well known in the art and are readily available from manufactures such as Millipore, Pall, Asahi Kasei, and Gambro. Preferably, the filters are made from materials that are biocompatible, such as polyethylene, polypropylene, PMMA, polysulfone, polyethersulfone, cellulose, silicon, ceramic, and the like. In embodiments, the first filter 20 comprises one or more membranes. In some embodiments, the first filter 20 comprises one or more hollow fibers.

Still with reference to FIGS. 1-3, the separated or filtered plasma is filtered via a second filter 30 to remove fluid. By way of example, fluid may be removed by filter 30 as typically done in ultrafiltration, hemofiltration, hemodialysis, or hemodiafiltration devices. Examples of such devices or components thereof that may be employed in accordance with the teachings presented herein are well known in the art. It will be understood that peritoneal dialysis, where dialysate is introduced into the peritoneal cavity, may also be employed. In embodiments where the blood fluid removal device or system, or components thereof, are implanted, the removed fluid may be diverted to the patient's bladder.

The second filter 30 may be any filter suitable for removal of fluid from plasma. By way of example, filters used in ultrafiltration, hemofiltration, hemodialysis, or hemodiafiltration may be employed. In embodiments, the second filter 30 has a molecular weight cut off of between about 10,000 and about 100,000 Da. Such filters should restrict or exclude passage of larger components of plasma to pass through the filter, while allowing fluid and smaller components (e.g., less than 60,000 Da), such as urea, creatinine, and the like, to pass through the filter. Such filters are well known in the art and are readily available from manufactures such as Gambro, Nipro, and Fresenius. Preferably, the filters are made from materials that are biocompatible, such as polysulfone, polyethersulfone, polyacrylonitrile, PMMA, and the like. In embodiments, the second filter 30 comprises one or more membranes. In some embodiments, the second filter 30 comprises one or more hollow fibers.

As shown in FIGS. 1-3, the reduced fluid plasma is combined with the cell enriched blood and returned to the patient 10. With some processes, devices or systems, fluid may be removed at too great of a rate or amount. As shown in FIG. 1, replacement fluid (RF) may be introduced to the patient's blood, cell enriched blood, plasma, reduced fluid plasma, or the like, before the reconstituted blood is returned to the patient. While not shown in FIGS. 2-3, it will be understood that replacement fluid may be added as described and shown with regard to FIG. 1. Replacement fluid may be tailored to adjust the pH, electrolyte concentrations, etc. so that blood returned to the patient has a desired composition.

As shown in the embodiment depicted in FIG. 2, dialysate may be employed to assist in removal of contaminants from the patient's plasma and in maintaining proper pH and electrolyte balance. Used dialysate and fluid removed from the blood may be diverted. In some embodiments, particularly where the blood fluid removal device or system or components thereof are wearable or implantable, the used dialysate and removed fluid, or a portion thereof, may be regenerated to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. Another system for regenerative dialysis has been described in U.S. Provisional Patent Application Ser. No. 61/480,532, entitled ELECTROLYTE AND pH MONITORING FOR FLUID REMOVAL PROCESSES, filed on Apr. 29, 2011, which application is hereby incorporated herein by reference to the extent that it does not conflict with the present disclosure presented herein. While not shown in FIGS. 1 and 3, it will be understood that dialysate may be used in these embodiments as described and shown with regard to FIG. 2.

Referring now to FIG. 3, plasma may be contacted with a sorbent medium 40 to selectively remove components from the plasma to produce sorbed plasma, which may be combined with cell enriched blood and returned to the patient 10. Selective removal of components from blood via a sorbent presents challenges due to clotting. However, by prefiltering the blood (via the first filter 20), cells and clotting factors may be removed or reduced, allowing for more efficient use of the sorbent 40 with plasma. The sorbent medium 40 may be configured to remove one or more waste or other products from plasma, such as urea, uric acid, β2-microglobulin, creatinine, phosphate, or the like. The sorbent medium 40 may include selective binding agents, such as antibodies, receptors, or the like, bound to membranes, fibers, particles, or the like to selectively remove targeted components from plasma. The sorbent medium may be contained in a packed column or in the flow path between the first 20 and second 30 filters. In embodiments, the sorbent medium contains materials such zirconium oxide, zirconium phosphate, activated carbon, zeolites, zirconium silicate, polymer resins, and the like. In embodiments, the sorbent medium 40 is included in a cartridge or other container or module.

As shown in FIG. 3, the plasma may be passed through or along the sorbent 40 before (dashed lines) or after (solid lines) fluid is removed from the plasma. While not shown in FIGS. 1-2, it will be understood that a sorbent may be similarly employed in those embodiments.

As further shown in FIGS. 1-3, some or all of the reduced fluid plasma that has passed through filter 30 may be recirculated back through filter 30 in a recirculation loop. A valve (not shown) or flow restrictor downstream of the recirculation loop (not shown) may be used to direct reduced fluid plasma into the recirculation loop. A recirculation loop may result in increased efficiency of fluid removal per surface area of filter 30. Use of a recirculation loop may also allow the filtration rate across the first filter 20 to be relatively low, which may allow use of a membrane having a smaller surface area and a lower blood flow rate, which may allow use of less anticoagulant. The recirculation rate could be relatively higher, e.g., between 50 ml/min to 200 ml/min to allow more efficient dialysis or filtration across the second membrane 30. To achieve the higher rates of flow in the recirculation loop, a pump (not shown) may be employed.

While not shown in FIGS. 1-3, it will be understood that the first 20 and second 30 filters may be disposed in a single housing, cartridge, container or the like. Sorbent 40 may also be disposed in the housing, cartridge, etc. Alternatively, the first 20 and second 30 filters and sorbent 40, if employed, may be disposed within separate housings, cartridges, containers, etc.

Figure 4:
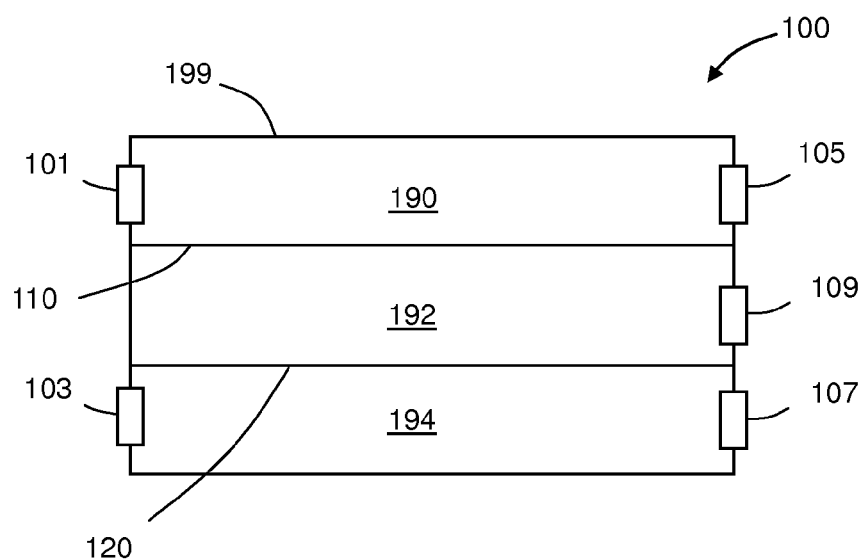
FIGS. 4-6 are schematic block diagrams of embodiments of blood fluid removal devices in accordance with embodiments described herein.

Referring now to FIGS. 4-6, schematic diagrams of blood fluid removal devices 100 are shown. The depicted devices 100 have a housing 199 defining an interior. The interior includes a blood compartment 190 through which blood and cell enriched blood (e.g., as described above with regard to FIGS. 1-3) may flow, a plasma compartment 192 through with plasma, reduced fluid plasma or sorbed plasma (e.g., as described above with regard to FIGS. 1-3) may flow, and a fluid compartment 194, through which fluid removed from plasma or dialysate may flow. A first filter 110 is disposed in the housing 199 and separates at least a portion of the blood compartment 190 from the plasma compartment 192. The first filter 110 in the embodiments may be a filter as described above with regard to the first filter 20 in FIGS. 1-3. That is, the first filter 110 is configured to allow plasma components, but not cell or larger components, of blood to pass through the filter from the blood compartment 190 to the plasma compartment 192.

The devices 100 in FIGS. 4-6 include an inlet 101 and an outlet 105 in fluid communication with the blood compartment. Blood from the patient may be introduced into the device 100 via inlet 101 and cell enriched blood may exit the device 100 via outlet 105.

The devices shown in FIGS. 4-6, include a second filter 120 disposed in the interior defined by the housing 199 and separates at least a portion of the plasma compartment 192 from the fluid compartment 194. The second filter 120 may be a filter as described above with regard to the second filter 30 in FIGS. 1-3. That is, the second filter 120 is configured to allow fluid and other small or dissolved components, but not larger components, of plasma to pass through the filter 120 from the plasma compartment 192 to the fluid compartment 194.

The devices depicted in FIGS. 4-6 include an outlet 107 in fluid communication with the fluid compartment, and may optionally contain an inlet 103 in fluid communication with the fluid compartment, as depicted. The inlet 103 may serve to allow dialysate and/or enrichment fluid to be introduced into the fluid compartment 194. Enrichment fluid may be fluid with predetermined concentrations of electrolytes, buffers, etc. to adjust the pH or electrolyte concentration of plasma in plasma compartment 192 across filter 120. The outlet 107 allows fluid removed from plasma, and used dialysate or enrichment fluid (if employed), to exit the device 100. While not shown, the plasma compartment 192 may have an inlet for purposes of priming.

Figure 5A:
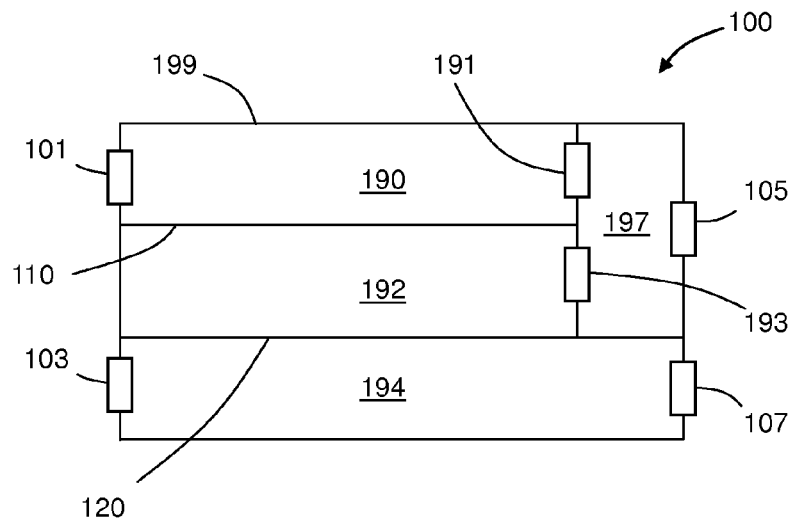

The device 100 may also include an outlet 109 in communication with the plasma compartment 192. Reduced fluid plasma may exit outlet 109 and be combined with cell enriched blood that exits outlet 105 prior to return to the patient. Alternatively, as depicted in FIG. 5A, the reduced fluid plasma and cell enriched blood may be combined prior to exiting device 100 via exit 105. In the embodiment depicted in FIG. 5A, cell enriched blood exits the blood compartment 190 via port or opening 191 and reduced fluid plasma exits the plasma compartment 192 via port or opening 193 to enter mixing chamber 197. Preferably, ports or openings 191, 193 contain one way valves to prevent fluid flow from the mixing chamber 197 to fluid compartment 190 or plasma compartment 192. The plasma and blood components may be mixed or combined within mixing chamber prior to exiting via outlet 105.

Figure 5B:
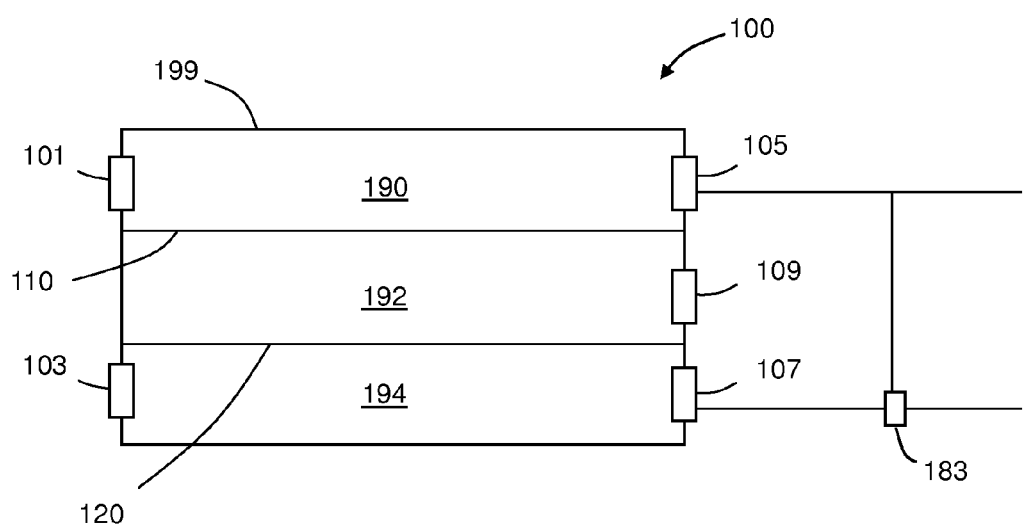

When too much fluid is removed from plasma, and thus the fluid levels of recombined blood is too low, it may be desirable or advantageous to add additional fluid to the blood before the blood is returned to the patient. In embodiments, fluid from the fluid compartment 190 is added prior to returning the blood to the patient. The fluid may be introduced into mixing chamber 197 or may be introduced into to recombined blood, plasma or cell-enriched blood at any suitable point. In embodiments and as shown in FIG. 5B, lines or conduits in communication with outlets 105, 107 may be used to divert a portion of fluid from fluid compartment 194 to blood before the blood is returned to the patient. A valve 183, flow restrictor, or the like, may be employed to divert all or a portion of the fluid to the blood.

Figure 6A:
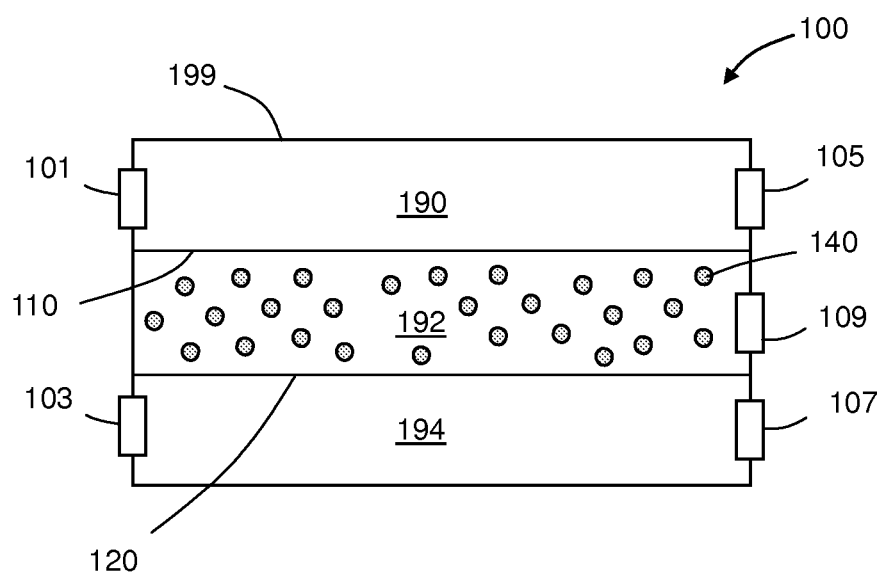
Figure 6B:
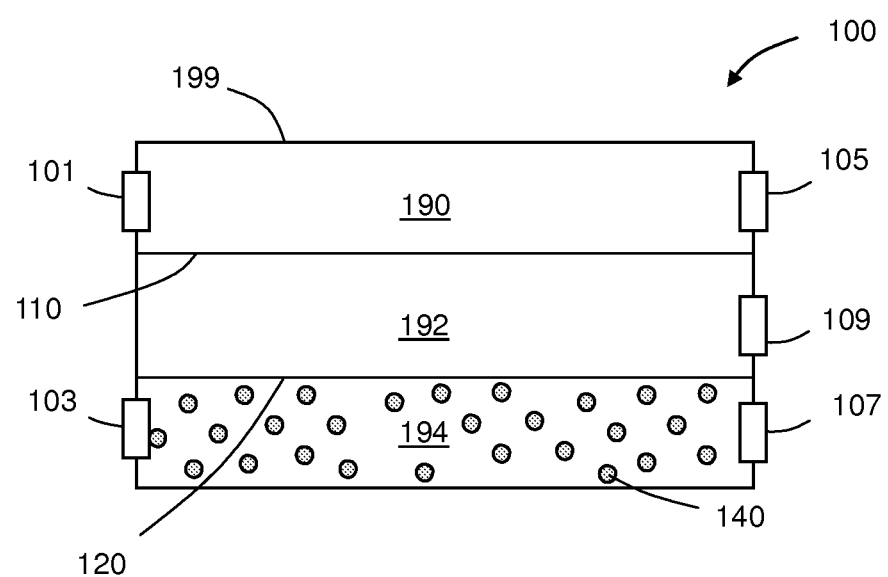

As depicted in FIG. 6A, a sorbent medium 40 may be disposed within the plasma compartment 192 to selectively remove components from plasma at the same time fluid is removed from plasma via second membrane 120. As depicted in FIG. 6B, a sorbent medium 40 may be disposed with the fluid compartment 194 to sorb components from fluid removed from the plasma. It may be desirable or advantageous to employ sorbent medium 40 in the fluid compartment 194 when fluid, or a portion thereof, is to be combined with blood prior to returning blood to the patient.

The housing 199 or other components of device that may contact blood, plasma, or dialysate are preferably biocompatible or may be coated with a biocompatible material. In embodiments, the housing is formed from a metallic material, such as stainless steel (or a suitable polymeric material, such as polystyrene, polycarbonate, or the like. If stainless steel components are employed, blood is preferably isolated from such components.

Referring now to FIGS. 7-14, embodiments of devices 100 or components thereof are depicted. The depicted devices 100 may operate in accordance with the general principles described above with regard to the devices of FIGS. 1-6. It will be understood that, while not necessarily shown, components of the devices or systems depicted with regard to FIGS. 1-6 may be employed with regard to the devices of FIGS. 7-15.

Figure 7:
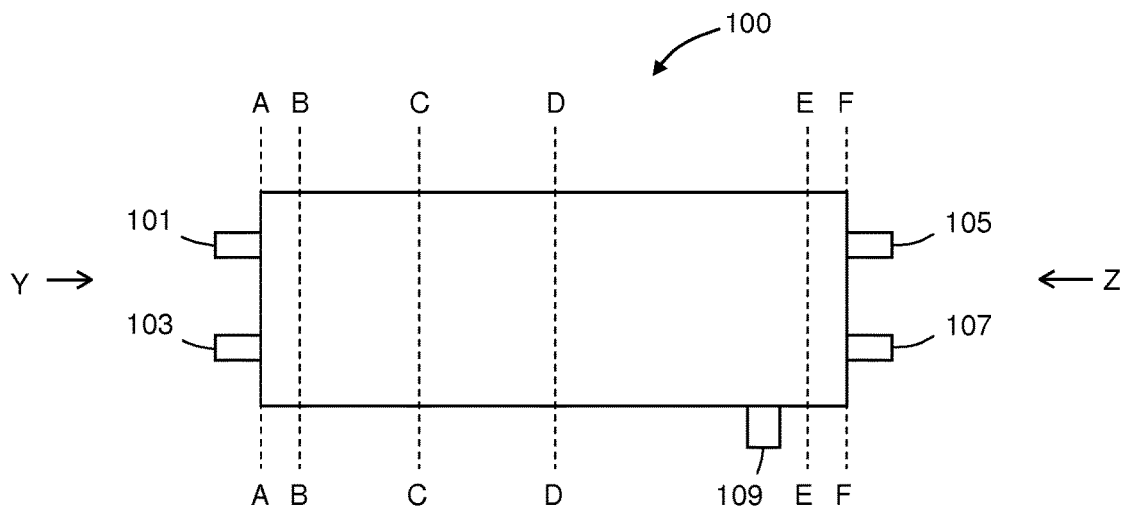
FIG. 7 is a schematic diagram of a side view of an embodiment of a blood fluid removal module in accordance with embodiments described herein.

As shown in FIG. 7, the device 100 may have inlets 101, 103 and outlets 105, 107, 109 as described above with regard to, e.g., FIGS. 4 and 6. The device 100 depicted in FIG. 7 is in the form of a cartridge or module, but may be in any other suitable form. In embodiments, the device 100 is cylindrical (not shown).

FIGS. 8-14 are schematic sectional views of embodiments of the device 100 shown in FIG. 7. In FIGS. 8A and 10-14, various embodiments of devices taken through lines C-C and D-D of FIG. 7 are shown, with the section taken through line C-C shown in front. FIGS. 8B-8E show front views (8B) and back views (8C-E) of sections of embodiments of manifold 150 taken through lines A-A (8B) and B-B (8C-E) of FIG. 7. FIGS. 8F-8I show back views (8G) and front views (8F, H, I) of embodiments of manifold 170 taken through lines E-E (8G) and F-F (8F, H, I).

Figure 8A:
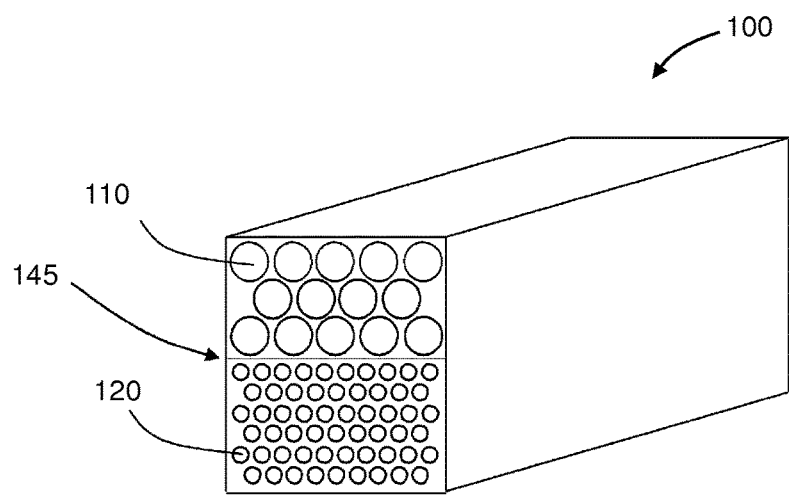
FIGS. 8A-K are schematic views of various embodiments of the module of FIG. 7, taken through various sections.

Referring now to FIG. 8A, the depicted blood fluid removal device 100 includes a plurality of hollow large pore fibers 110 configured to allow plasma components, but not cell components, of blood to pass. Accordingly, the large pore fibers 110 may function as first filter 110 as discussed above with regard to FIG. 5. Blood may be introduced into lumens of the porous fibers 110 (and thus the lumens of the fibers 110 would constitute the blood compartment 190 as described above with regard to FIG. 5). Plasma may pass through the pores of the fibers 110 and be located exterior to the fibers (and thus at least a portion of the plasma compartment 192 as described above with regard to FIG. 5 would be located exterior to the large pore fibers 110 in FIG. 8A).

Alternatively, blood may be introduced into the device 100 exterior to the porous fibers 110 and plasma may pass through the pores of the fiber and enter the lumens of the fibers 110. Thus, at least a portion of the plasma compartment would be defined by the lumens of the fibers 110, and the blood compartment would be defined exterior to the fibers 110. In such an embodiment, the device 145 preferably includes a dividing member 145, such as a wall (e.g., a wall impermeable by blood), to separate the large pore fibers 110 from the small pore fibers 120 and to isolate compartment containing fibers 110.

The small pore fibers 120 depicted in FIG. 8A are configured to allow fluid and smaller components, but not larger plasma components, of plasma to pass. Accordingly, the small pore fibers 120 may function as second filter 120 as discussed above with regard to FIG. 5. In embodiments, at least a portion of the plasma compartment (e.g., compartment 192 discussed with regard to FIG. 5) is defined by the space immediately surrounding the small porous fibers 120. In such embodiments, fluid from the plasma may cross the walls of the fibers to enter the lumen of the fibers 120. Thus, the lumen of the fibers 120 constitutes the fluid compartment (e.g., compartment 194 discussed above with regard to FIG. 5). In such embodiments, the device 100 preferably does not include dividing member 145, if the blood compartment is defined by the lumens of the large pore fibers 110. Thus plasma from blood in the lumen of the large fiber 110 may flow through the wall of the fiber 110 to the exterior of the large fibers 110 and surround the small fibers 120 so that fluid may flow into the lumens of the small fibers 120 for removal.

In embodiments, plasma is directed into the lumens of the small pore fibers 120. Thus, at least a portion of the plasma compartment is defined by the lumens of the porous fibers 120. The fluid compartment would then be exterior to the small pore fibers 120.

Figure 8B:
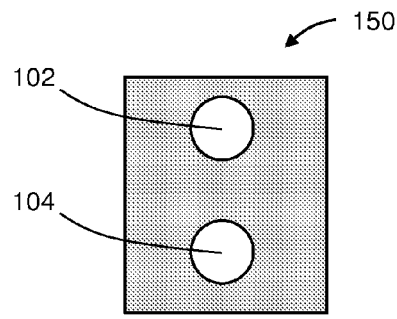

FIGS. 8B-K show various embodiments of sections of manifolds 150 (e.g. encompassing at least the portion of the device in FIG. 7 between lines A-A and B-B), that may be used to direct blood or dialysate, if used, to an appropriate compartment (i.e., blood or fluid compartment) of a device as described with regard to FIG. 8A. As shown in FIG. 8B, the front of the manifold 150 (e.g., section A-A of FIG. 7 when viewed in the direction indicated by arrow Y) includes first 102 and second 104 openings. The first opening 102 is in communication with port or inlet 101 depicted in FIG. 7 for introducing blood into the device. The second opening 104 is in communication with port or inlet 103 depicted in FIG. 7 for introducing dialysate into the device.

Figure 8C:
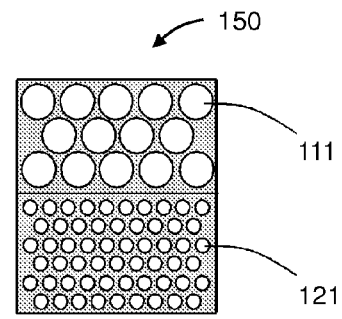

FIGS. 8C-G show alternative back portions (e.g., section B-B of FIG. 7 when viewed in the direction indicated by arrow Z) of the manifold of FIG. 8B for appropriately directing the blood or dialysate into the device of FIG. 8A. As shown in FIG. 8C, the manifold may have a plurality of openings 111 in communication with opening 102 of FIG. 8B. The openings 111 are configured and positioned to allow blood to flow into the lumens of the large pore fibers 110 depicted in FIG. 8A. As further shown in FIG. 8C, the manifold may have a plurality of openings 121 in communication with opening 102 of FIG. 8B. The openings 121 are configured and positioned to allow dialysate to flow into the lumens of the small pore fibers 120 depicted in FIG. 8A. The fibers may be sealed to the manifold such that the lumens of the fibers are in communication with the appropriate openings 111, 121 of the manifold 150. The fibers may be sealed to the manifold in any suitable manner, such as via a polymeric material (e.g., an epoxy resin or the like).

Figure 8D:
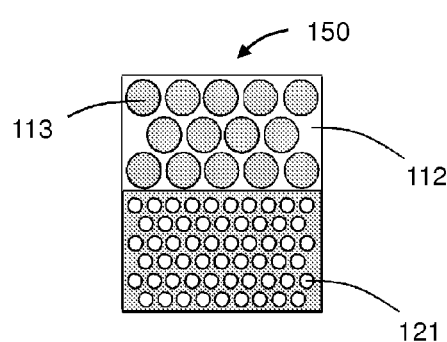
Figure 8E:
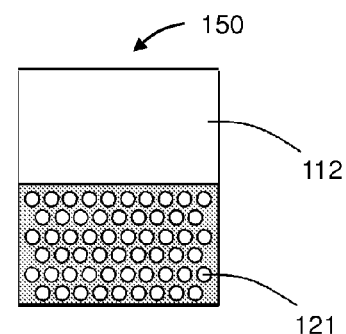

In the embodiments depicted in FIG. 8D, the open area 112 of the manifold, which is in communication with opening 102 depicted in FIG. 8B, is configured and positioned to allow blood to flow external to large pore fibers 110 of FIG. 8A. In this embodiment, solid elements 113 of manifold 150 are sealed to ends of large pore fibers 110 (e.g. via an appropriate polymer) to isolate the lumens of the large pore fibers from the blood. Alternatively, the ends of the large pore fibers may be sealed, such as by potting in the ends with an appropriate polymeric material, such as an epoxy resin. In such cases, the back portion of the manifold 150 in communication with opening 102 (see, FIG. 8B), which is the upper portion in FIG. 8E, may include one large opening 112.

Figure 8F:
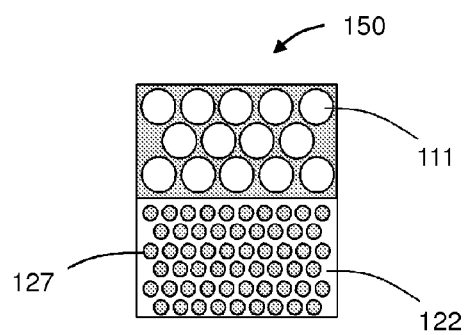
Figure 8G:
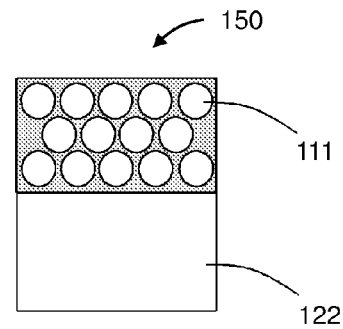

In the embodiment depicted in FIG. 8F, the open area 122 of the manifold, which is in communication with opening 104 depicted in FIG. 8B, is configured and positioned to allow dialysate to flow external to small pore fibers 120 of FIG. 8A. In this embodiment, solid elements 127 of manifold 150 are sealed to ends of small pore fibers 120 to isolate the lumens of the small pore fibers from the dialysate; e.g., as described above with regard to the large pore fibers with regard to blood. As shown in FIG. 8G the open area 112 may include one large opening 112 if the ends of the small pore fibers are sealed or potted.

Figure 8H:
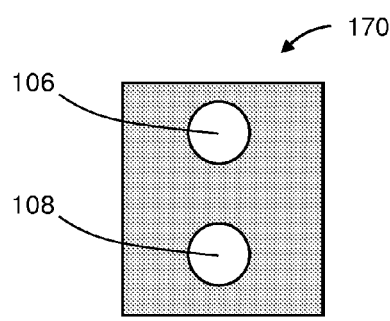
Figure 8I:
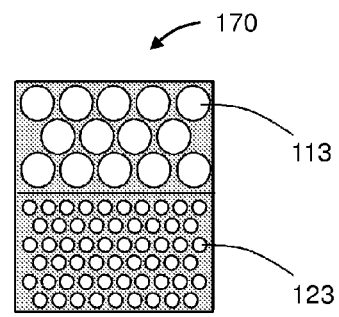

FIGS. 8H-8I depict an embodiment of sections of manifolds 170 (e.g. encompassing at least the portion of the device in FIG. 7 between lines E-E and F-F) that may be used to direct blood or fluid (or fluid and dialysate, if used) out of the device 100 shown in FIG. 8A, which is an embodiment of the device shown in FIG. 7. As shown in FIG. 8H, the back of the manifold 170 (e.g., section F-F of FIG. 7 when viewed in the direction indicated by arrow Z) includes first 106 and second 108 openings. The first opening 106 is in communication with port or outlet 105 depicted in FIG. 7 for removal of cell enhanced blood from the device. The second opening 108 is in communication with port or outlet 107 depicted in FIG. 7 for removal of fluid or fluid and used dialysate from the device. FIG. 8I depicts a front portion (e.g., section E-E of FIG. 7 when viewed in the direction indicated by arrow Y) of manifold 170. The depicted manifold 170 has a plurality of openings 113 in communication with opening 106 of FIG. 8H. The openings 113 are configured and positioned to allow blood to flow from the lumens of the large pore fibers 110 depicted in FIG. 8A through the manifold 170 (and thus the fibers are sealed relative to the manifold such that the lumen of the fibers are in communication with the openings 113). As further shown in FIG. 8I, the manifold may have a plurality of openings 123 in communication with opening 108 of FIG. 8H. The openings 123 are configured and positioned to allow fluid or fluid and used dialysate to flow out of the lumens of the small pore fibers 120 depicted in FIG. 8A and through the manifold (and thus the fibers are sealed relative to the manifold such that the lumen of the fibers are in communication with the openings 123).

Figure 8J:
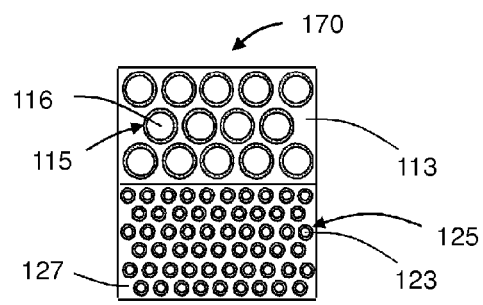
Figure 8K:
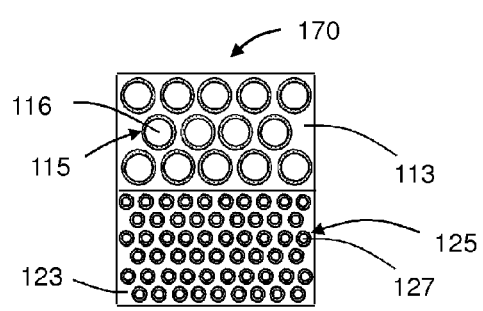

FIGS. 8J-K show alternative front portions (e.g., section E-E of FIG. 7 when viewed in the direction indicated by arrow Y) of manifold 170, for which the back portion is shown in FIG. 8H, for appropriately directing the blood or fluid out of the device of FIG. 8A. As shown in FIG. 8J, the manifold 170 may have an opening 113 in communication with opening 106 of FIG. 8H. The opening 113 is configured and positioned to allow blood exterior to the lumens of the large pore fibers 110 depicted in FIG. 8A to flow through the manifold 170 through the opening 113 and out opening 106 (see FIG. 8H). As further shown in FIG. 8J, the manifold 170 may have a plurality of diverter conduits 115 defining openings 116 through which plasma within pores of large pore fibers may be diverted into the lower portion of manifold and back into the device through opening 127 (and this the large pore fibers are sealed relative to conduits 115 such that the lumens of the fibers are in communication with openings 116). In the depicted embodiment, opening 127 is formed around structural elements 125 of the manifold 170. The structural elements define openings 123 in communication with opening 108 (see FIG. 8H). The openings 123 are configured and positioned to allow fluid or fluid and used dialysate to flow out of the lumens of the small pore fibers 120 depicted in FIG. 8A and through the manifold (and thus the small pore fibers are sealed relative to the structural elements 125 such that the lumens of the fibers are in communication with the openings 123).

In the embodiment depicted in FIG. 8K, the open area 123 of the manifold 170, which is in communication with opening 108 depicted in FIG. 8G, is configured and positioned to allow to dialysate from the outside of the small pore fibers 120 of FIG. 8A to flow through the manifold and out of the device. The open area 123 is defined around structural elements 125 which define openings 127, through which plasma is configured to flow back into the device. The top portion of the manifold 170 in FIG. 8K is the same as the top portion of the manifold in FIG. 8J. The manifold 170 is configured such that plasma within the diverter conduits 115 is diverted back into device through open area 123 (e.g., openings 116 defined by structural members 115 are in communication with open area 123.

It will be understood that manifold configurations other than those depicted in FIGS. 8B-K may be used to direct blood, fluid or dialysate to, or from, appropriate compartments of a blood fluid removal device 100 as depicted in FIG. 8A.

Figure 9:
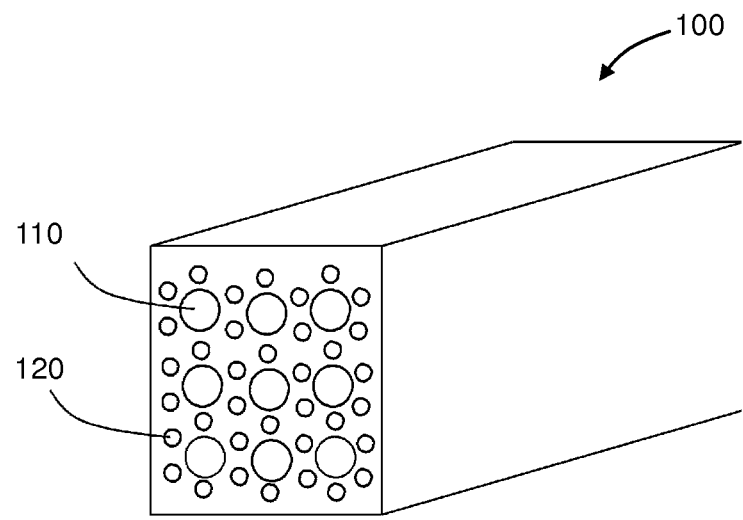
FIGS. 9-13 are partial sectional views of alternative embodiments of a blood fluid removal module taken through line C-C of FIG. 7.

Referring now to FIG. 9, an alternative embodiment of a device is shown. In the depicted embodiment, large pore fibers 110 and small pore fibers 120 are interspersed. Such an arrangement of fibers may be advantageous when the space surrounding the fibers is the plasma compartment (the blood compartment is within the lumens of the large pore fibers 110, and the fluid compartment is within the lumens of the small pore fibers 120). Any suitable manifold may be used to direct blood and dialysate, if used, into or out of the large 110 and small 120 pore fibers.

Figure 10:
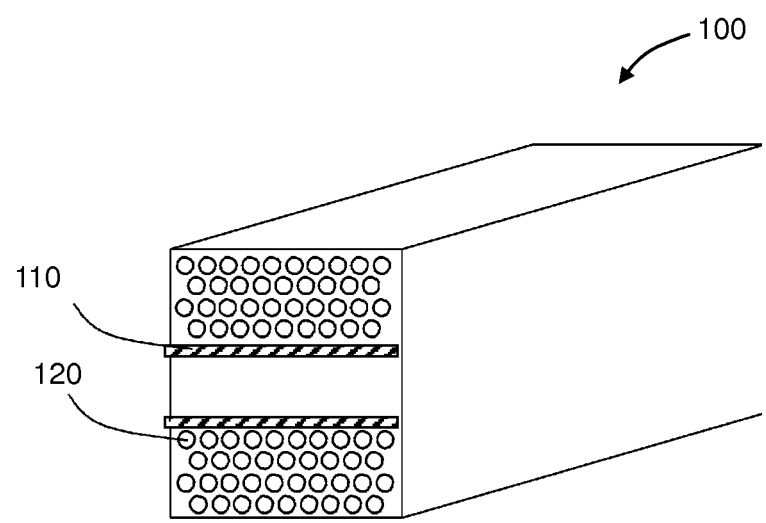

FIG. 10 illustrates an alternative embodiment, where a membrane 110 is disposed with and across the housing of the device 100. In the depicted embodiment, the membranes 100 are configured to allow plasma components, but not cell components, of blood to pass. Accordingly, the membrane 110 may function as first filter 110 as discussed above with regard to FIG. 5. In the embodiment depicted in FIG. 10, blood may be introduced between the membranes 110 (and thus the space between the membranes 110 would constitute the blood compartment 190 as described above with regard to FIG. 5). Plasma may pass through the membranes 110 and surround the small pore fibers 120, which may be small pore fibers as described above. Thus, fluid may pass from plasma into the lumens of the hollow porous fibers 120 or dialysate may be introduced into the lumens of the hollow porous fibers, e.g. as discussed above with regard to other embodiments.

Figure 11:
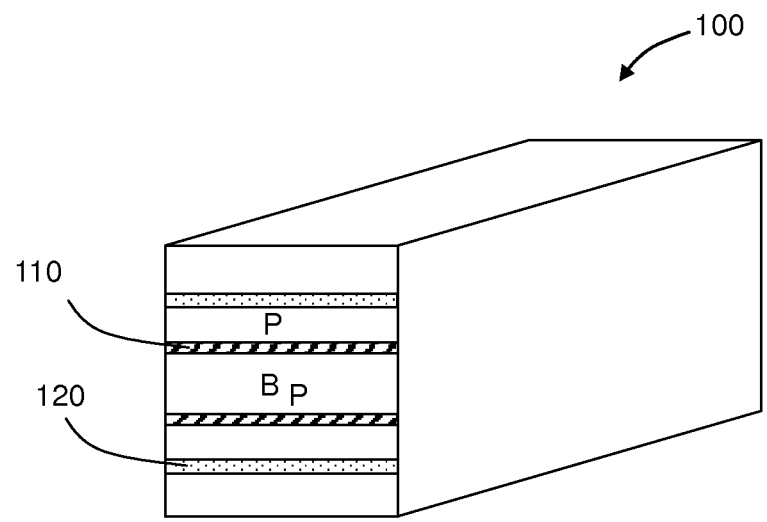

An alternative embodiment of a device 100 is depicted in FIG. 11. As shown, the device 100 may include membranes 110 that span the housing of the device and define the blood compartment B. Plasma may pass the membranes 110. In this embodiment, the plasma compartment P is defined between membranes 110 and membranes 120. Membranes 120 also span the housing and are configured to allow fluid and smaller components, but not larger plasma components, of plasma to pass. Accordingly, the membranes 120 may function as second filter 120 as discussed above with regard to FIG. 5. In the depicted embodiment, the fluid compartment is defined between the housing of the device and membranes 120 (at the topmost and bottommost portions of the depicted device).

Figure 12:
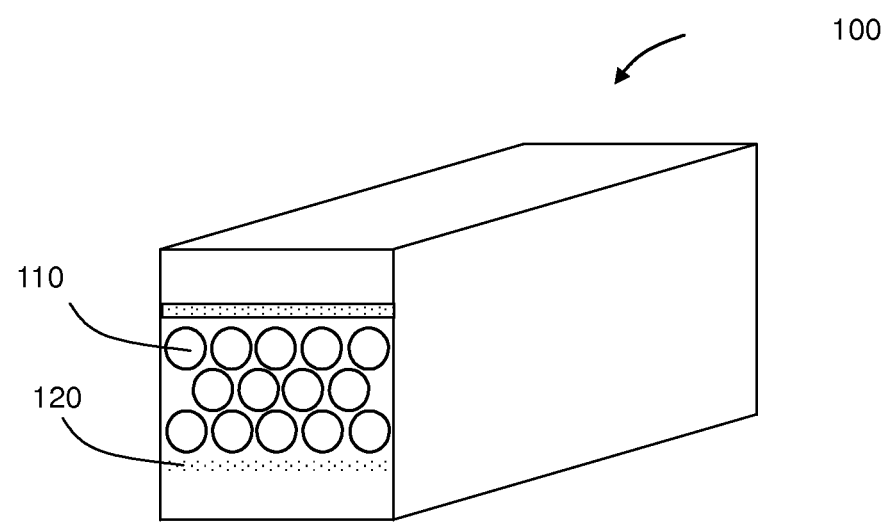

Another embodiment is depicted in FIG. 12, where blood is passed through lumens of large pore fibers 110 (e.g., as described above with regard to other embodiments). Plasma may pass through the porous walls of the fibers 110 to the space exterior to the fibers. Fluid from plasma may cross membrane 120 which is disposed across the housing of the device 100.

Figure 13:
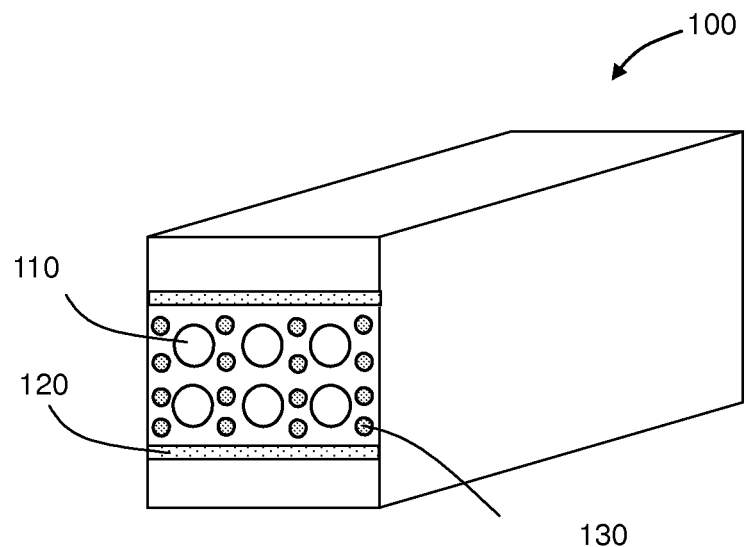

Yet another embodiment is depicted in FIG. 13. The device 100 depicted in FIG. 13 is similar to the device depicted in FIG. 12. However, the device 100 depicted in FIG. 14 includes sorbent material 130 disposed in the plasma compartment. Thus, selected components may be removed from plasma at the same time that fluid is removed from plasma across membrane 120. Sorbent material 130 may be sorbent material described above with regard to FIG. 3. While not shown, it will be understood that sorbent may be similarly placed in the plasma compartment of any of the other embodiments of devices 100 described above.

With regard to the embodiments shown in FIGS. 9-13, it will be understood that suitable manifolds may be employed to direct blood, fluid, dialysate, or plasma to or from the appropriate location or compartment of the device. It will also be understood that the embodiments depicted in FIGS. 8-13 are merely illustrative of possible embodiments and that combinations of elements depicted in these figures, which combinations are not shown or described herein, may be readily made and are contemplated. It will be further understood that modification of elements described herein may be made without departing from the scope or spirit of the devices, systems and methods described herein.

Referring now to FIGS. 14-18, schematic diagrams are shown that illustrate some principles of operation of embodiments of the devices described above. In the embodiments depicted, first 110 and second 120 filters are disposed within interior 180 of housing 199 of device 100. The filters 110, 120 may be fibers or membranes, but are shown as fibers for purposes of convenience. The interior 180 may be divided into first 182 and second 184 chambers in some embodiments (see, e.g., FIGS. 15-17). In the depicted embodiments, "B" refers to blood within the blood compartment, "P" refers to plasma within the plasma compartment, and "D" refers to dialysate in the fluid compartment. It will be understood that, while dialysate is shown in each of FIGS. 15-18, similar principles apply when dialysate is not used.

Figure 14:
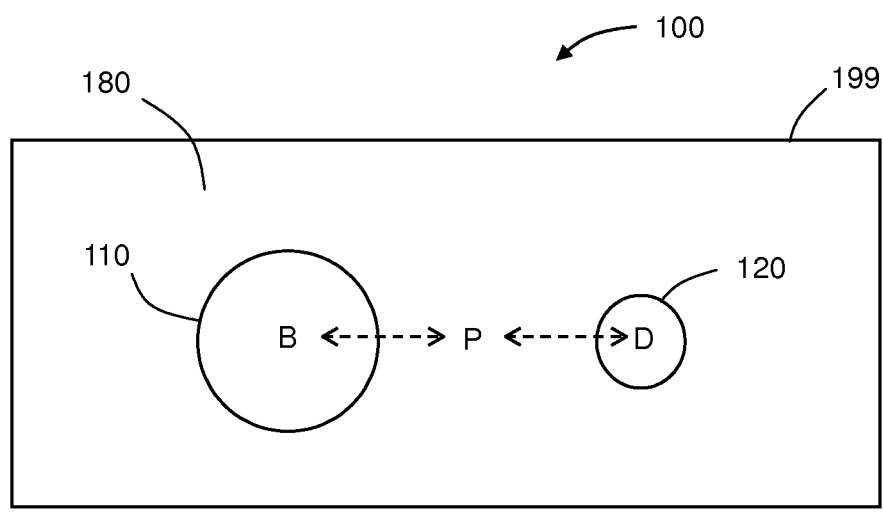
FIGS. 14-18 are schematic diagrams illustrating principles by which various embodiments of devices, systems and methods described herein may operate.

Referring now to FIG. 14, blood B is shown in a lumen of a large pore fiber 110. Plasma P may cross the wall of the porous fiber 110 and enter the space with the interior 180 of the housing 199 surrounding the large pore fibers 110 and the small pore fibers 120. Dialysate D flows through the lumen of the small pore fiber 120. Fluid and other agents may exchange between plasma P and dialysate D through the walls of the porous fiber 120. Thus fluid, and possibly waste products, is removed from plasma P, which may also have adjusted pH, buffers, electrolytes, etc. if dialysate is used as shown. The reduced fluid plasma P may then be combined with cell enriched blood B that flows through the device 100 before being returned to a patient, or the plasma, or some percentage thereof, may be recirculated and become equilibrated with the blood in terms of protein content, but still allow fluid to transfer from the blood to the plasma and out fiber 120. In FIG. 14 and FIGS. 15-18 that follow, the arrow between B and P is shown as bidirectional because plasma, or components thereof, may cross between plasma and blood compartments, with equilibrium being driven by pressure and concentration gradients.

Figure 15:
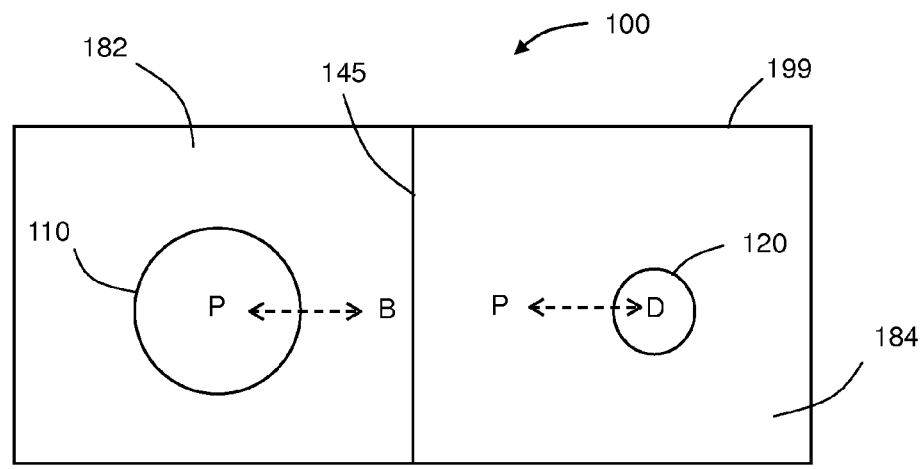

Referring now to FIG. 15, blood B is introduced exterior to the large pore fiber 110 in the first chamber 182. Plasma P may flow across the wall and into the lumen of the porous fiber 110. The plasma P is then directed to exterior to the small pore fiber 120 in the second chamber 184, e.g., via a manifold as described above, where fluid from plasma P may cross the wall, and enter the lumen, of the porous fiber 120. As shown, dialysate D may flow through the lumen of the small pore fiber 120 if desired.

Figure 16:
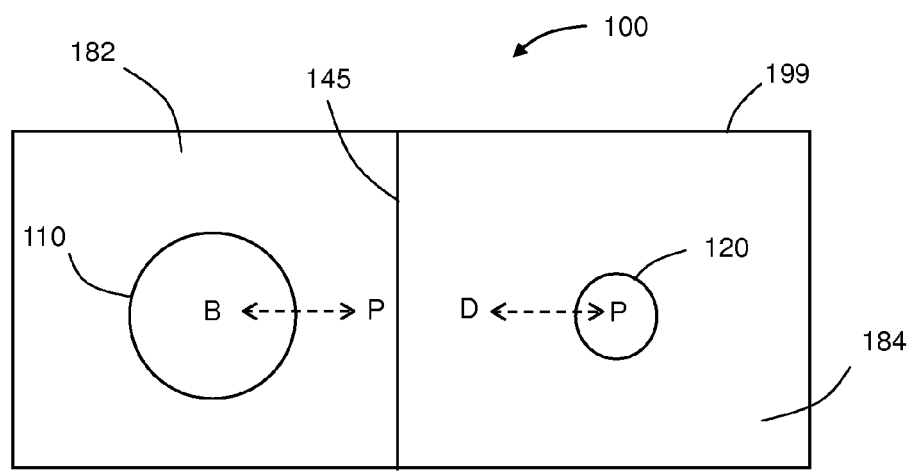

Referring now to FIG. 16, blood B is introduced into the lumen of the large pore fiber 110 in the first chamber 182. Plasma P may flow across the wall and into the first chamber 182 in the space surrounding the porous fiber 110. The plasma P is then directed to into the lumen of the small pore fiber 120 in the second chamber 184, e.g., via a manifold as described above, where fluid from plasma P may cross the wall, and enter the second chamber 184 in the space surrounding the porous fiber 120. As shown, dialysate D may flow the second chamber 184 in the space surrounding the small pore fiber 120 if desired.

Figure 17:
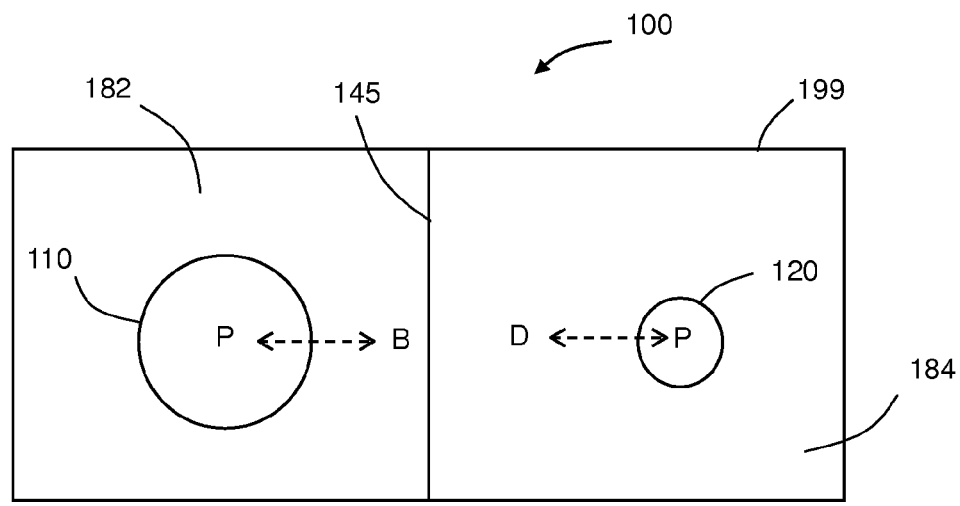

Referring now to FIG. 17, blood B is introduced exterior to the large pore fiber 110 in the first chamber 182. Plasma P may flow across the wall and into the lumen of the porous fiber 110. The plasma P is then directed to into the lumen of the small pore fiber 120 in the second chamber 184, e.g., via a manifold as described above, where fluid from plasma P may cross the wall, and enter the second chamber 184 in the space surrounding the porous fiber 120. As shown, dialysate D may flow the second chamber 184 in the space surrounding the small pore fiber 120 if desired.

Figure 18:
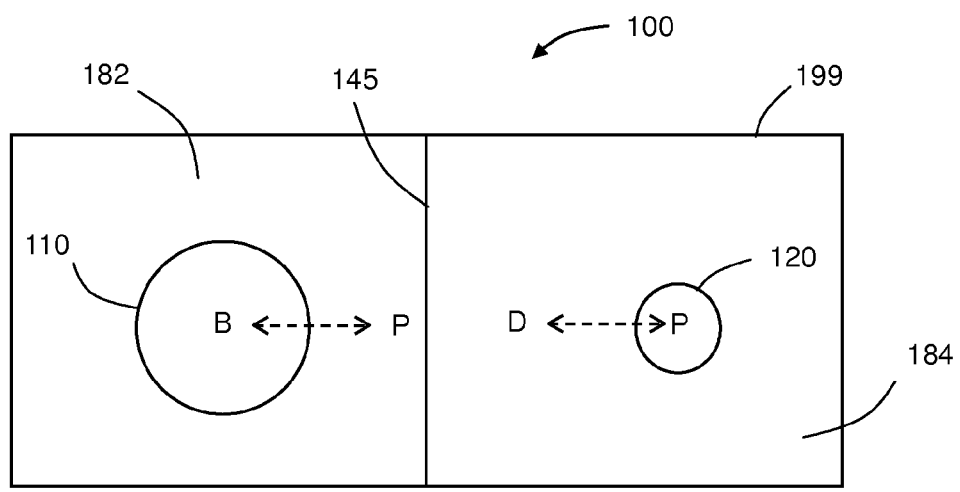

Referring now to FIG. 18, blood B is introduced into lumens of the large pore fibers 110. Plasma P may flow across the wall of the large pore fibers 110 and into in the first chamber 182. The plasma P is then directed to into the lumen of the small pore fiber 120 in the second chamber 184, e.g., via a manifold as described above, where fluid from plasma P may cross the wall, and enter the second chamber 184 in the space surrounding the porous fiber 120. As shown, dialysate D may flow the second chamber 184 in the space surrounding the small pore fiber 120 if desired.

It will be understood that FIGS. 14-18 represent only some examples of ways in which plasma may be separated from blood and fluid may be removed from the plasma and that other ways of accomplishing separating plasma from blood prior to fluid removal from plasma are contemplated herein. It will also be understood that sorbent may be placed at any suitable location in the plasma compartment, either upstream or downstream of fluid removal. For example, (i) if blood is introduced external to large pore fibers so that plasma flows into the lumens of the fibers, sorbent may be place in the lumens of the fibers; (ii) if blood is introduced into the lumens of the large pore fibers, sorbent may be placed in the space external to the large pore fibers; (iii) if plasma is introduced into lumens of the small pore fibers, sorbent may be placed in the lumens of the small pore fibers; (iv) if plasma is introduced into the space surrounding the small pore fibers, sorbent may be placed in the space around the small pore fibers; (v) etc.

Figure 19:
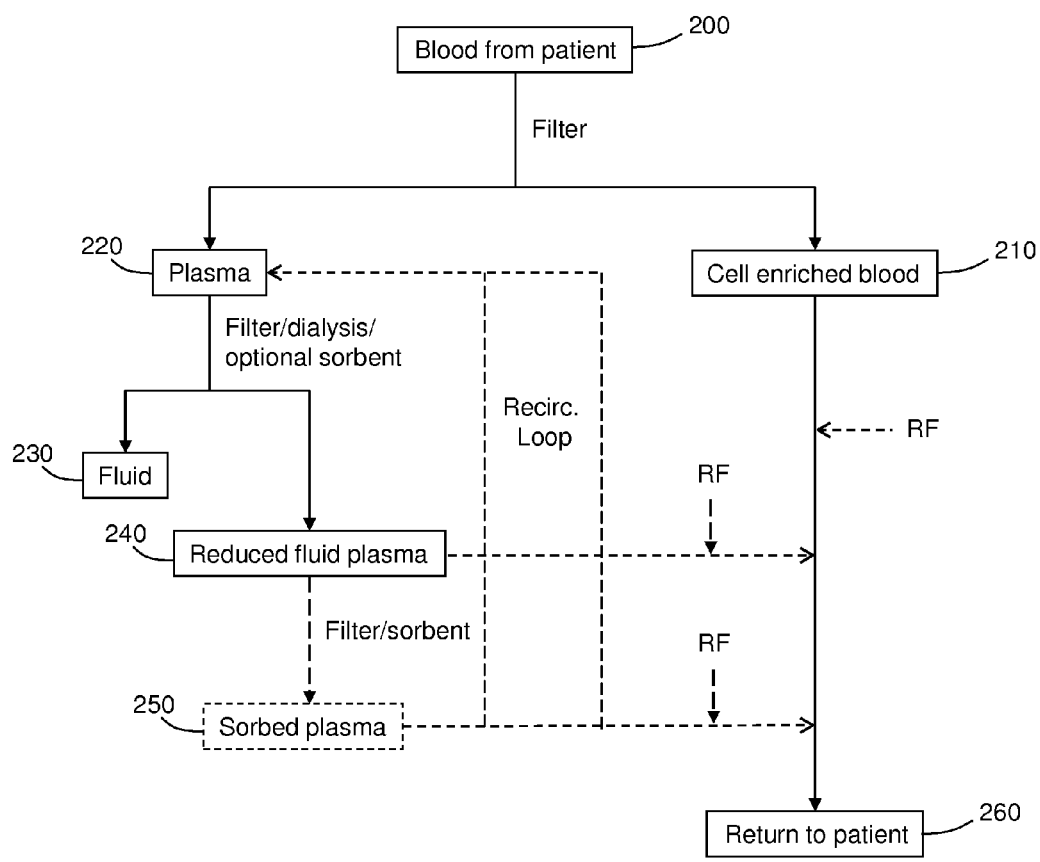
FIG. 19 is a schematic overview for removing plasma from blood and removing fluid from the plasma according to embodiments described herein.

Referring now to FIG. 19, an overview of a scheme for separating plasma from blood and removing fluid from the separated plasma is shown. Any suitable device or system for accomplishing this scheme may be used in accordance with the teachings herein. In the depicted scheme, blood from the patient 200 is filtered to separate cell enriched blood 210 and plasma 220. The plasma 220 is then filtered or dialyzed (and optionally sorbed) to remove fluid 230 from the plasma and leave reduced fluid plasma 240. The reduced fluid plasma 240 may be further filtered or contacted with a sorbent to produce sorbed plasma 250. The reduced fluid plasma 240 or sorbed plasma 250 is then combined with the cell enriched blood 210 and returned to the patient 260. In addition or alternatively, the reduced fluid plasma is recirculated and further subjected to filtering, dialysis or sorption. Replacement or enrichment fluid RF may be added to reduced fluid or sorbed plasma or cell-enriched blood prior to returning the reduced-fluid blood to the patient. While not shown, it will be understood that some or all of the fluid 230 removed from plasma 220 may be returned to blood (e.g., added to cell enriched blood 210 or reduced fluid plasma 240) prior to returning to the patient 260. In such situations it may be desirable to remove waste products from the fluid 230 by sorption.

Figure 20:
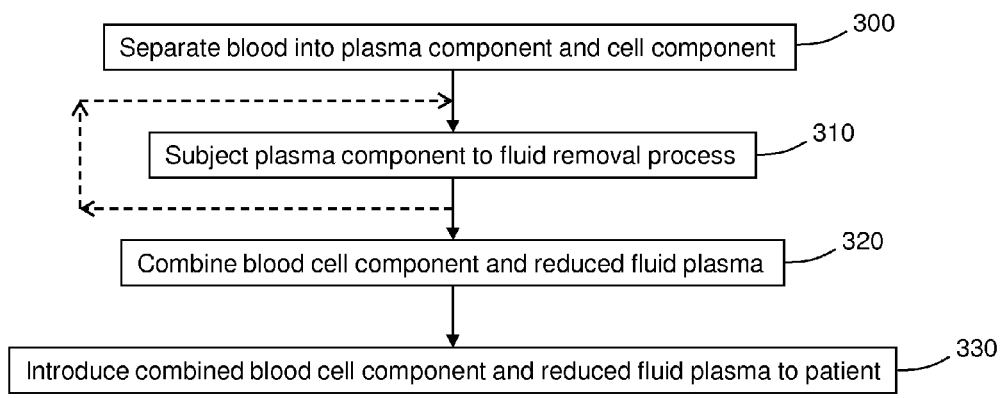
FIGS. 20-21 are flow diagrams illustrating embodiments of methods described herein.
Figure 21:
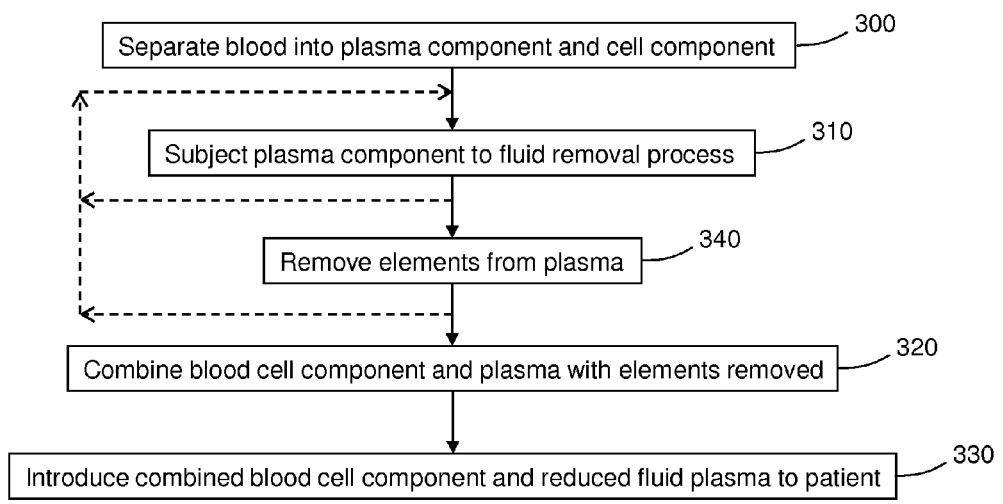

Referring now to FIGS. 20 and 21, overviews of methods are depicted. The methods summarize many of the concepts described above. In FIG. 20, the method includes separating blood in a plasma component and a blood component (300); e.g. with a large pore filter. The method further includes subjecting the plasma component to a fluid removal process (310), such as ultrafiltration or hemodialysis via a small pore filter. The separated blood component and the plasma with fluid removed are combined (320) and returned to the patient (330). In addition, or alternatively, the reduced fluid plasma may be recirculated to undergo further fluid removal as indicated by the dashed lines in FIG. 20.

The method in FIG. 21 is similar to the method depicted in FIG. 20, but further includes removing elements from plasma (340). While this is shown in FIG. 21 as occurring after the plasma is subjected to the fluid removal process (310), it will be understood that elements may be removed from plasma (340) prior to or during the fluid removal process (310). The dashed lines in FIG. 21 indicate optional recirculation of reduced-fluid plasma, or a percentage thereof (e.g., as described with regard to FIG. 20).

A summary of selected aspects of methods, devices and systems described herein is provided below.

In a first aspect, a medical device includes (i) a housing defining an interior, wherein the interior has a blood compartment, a plasma compartment, and a fluid compartment; (ii) a first filter disposed in the interior of the housing, wherein the first filter separates at least a portion of the blood compartment from at least a portion of the plasma compartment and wherein the first filter is configured to allow plasma components, but not cell components, of blood to pass through the first filter from the blood compartment to the plasma compartment; and (iii) a second filter disposed in the interior of the housing, wherein the second filter separates at least a portion of the plasma compartment from at least a portion of the fluid compartment, wherein the second filter is configured to allow fluid and small molecules, but not larger components, to pass through the second filter from the plasma compartment to the fluid compartment.

A second aspect is a device of the first aspect, further comprising: (i) an inlet in communication with the blood compartment; (ii) a first outlet in communication with the blood compartment; and (iii) a second outlet in communication with the fluid compartment.

A third aspect is a device of the second aspect, wherein the first outlet is in communication with the plasma compartment.

A fourth aspect is a device of the second aspect, further comprising a third outlet in communication with the plasma compartment.

A fifth aspect is a device of any of the first four aspects, further comprising a dialysate inlet in communication with the fluid compartment.

A sixth aspect is a device of any of the first five aspects, wherein the first filter comprises a porous fiber having a lumen, and wherein at least a portion of the blood compartment is defined by the lumen of the first filter porous fiber.

A seventh aspect is a device according to the sixth aspect, wherein the second filter comprises a porous fiber having a lumen, and wherein at least a portion of the fluid compartment is defined by the lumen of the second filter porous fiber.

An eighth aspect is a device according to the sixth aspect, wherein the second filter comprises a porous fiber having a lumen, and wherein at least a portion of the plasma compartment is defined by the lumen of the second filter porous fiber.

A ninth aspect is a device according to the eighth aspect, wherein a first portion of the plasma compartment is defined by the exterior of the first filter porous fiber, and wherein the device further comprises a manifold having at least one opening in communication with the first portion of the plasma compartment and the lumen of the second filter porous fiber.

A tenth aspect is a device according to the sixth aspect, wherein the second filter comprises a membrane.

An eleventh aspect is a device according to the tenth aspect, wherein the membrane is disposed across the housing.

A twelfth aspect is a device according to any of the first five aspects, wherein the first filter comprises a porous fiber having a lumen, and wherein at least a portion of the plasma compartment is defined by the lumen of the first filter porous fiber.

A thirteenth aspect is a device according to the twelfth aspect, wherein the second filter comprises a porous fiber having a lumen, and wherein at least a portion of the fluid compartment is defined by the lumen of the second filter porous fiber.

A fourteenth aspect is a device according to the twelfth aspect, wherein the second filter comprises a porous fiber having a lumen, and wherein at least a portion of the plasma compartment is defined by the lumen of the second filter porous fiber.

A fifteenth aspect is a device according to the fourteenth aspect, further comprising a manifold having at least one opening in communication with the lumen of the first filter porous fiber and the lumen of the second filter porous fiber.

A sixteenth aspect is a device according to the twelfth aspect, wherein the second filter comprises a membrane.

A seventeenth aspect is a device according to the sixteenth aspect, wherein the membrane is disposed across the housing.

An eighteenth aspect is a device according to any of the first five aspects, wherein the first filter comprises a membrane.

A nineteenth aspect is a device according to the eighteenth aspect, wherein the membrane is disposed across the housing.

A twentieth aspect is a device according to the eighteenth or nineteenth aspects, wherein the second filter comprises a porous fiber having a lumen, and wherein at least a portion of the fluid compartment is defined by the lumen of the second filter porous fiber.

A twenty-first aspect is a device according to the eighteenth or nineteenth aspects, wherein the second filter comprises a porous fiber having a lumen, and wherein at least a portion of the plasma compartment is defined by the lumen of the second filter porous fiber.

A twenty-second aspect is a device according to according to the eighteenth or nineteenth aspects, wherein the second filter comprises a membrane.

A twenty-third aspect is a device according to the twenty-second aspect, wherein the membrane is disposed across the housing.

A twenty-fourth aspect is a device according to any of the first twenty-three aspects, further comprising a sorbent disposed within the plasma compartment, wherein the sorbent is configured to selectively absorb one or more components from plasma.

A twenty-fifth aspect is a device according to any of the first twenty-four aspects, wherein the device is in the form of a cartridge.

A twenty-sixth aspect is a system including (i) a device according to any of aspects 1-25, wherein the device comprises the third outlet of aspect 4; and (ii) a sorbent medium in fluid communication with the plasma compartment of the device and downstream of the third outlet.

A twenty-seventh aspect is a system according to the twenty-sixth aspect, further comprising a manifold having a first inlet in communication with the blood compartment of the device, a second inlet in communication with the plasma compartment of the device and downstream of the sorbent medium, and an outlet in communication with the first and second manifold inlets.

A twenty-eighth aspect is a method including (i) separating a patient's blood into a plasma component and a cell component; (ii) dialyzing the plasma component to obtain dialyzed plasma; and (iii) combining the cell component and the dialyzed plasma to generate dialyzed blood.

A twenty-ninth aspect is a method according to the twenty-eighth aspect, further comprising introducing the dialyzed blood into the patient.

A thirtieth aspect is a method according to the twenty-eighth or twenty-ninth aspects, further comprising removing selected elements from the plasma component via a sorbent.

A thirty-first aspect is a method according to the twenty-eighth or twenty-ninth aspects, further comprising removing selected elements from the dialyzed plasma via a sorbent.

A thirty-second aspect is a method including (i) separating a patient's blood into a plasma component and a cell component; (ii) filtering fluid from the plasma component to obtain reduced fluid plasma; and (iii) combining the cell component and the reduced fluid plasma to generate filtered blood.

A thirty-third aspect is a method according to the thirty-second aspect, further comprising introducing the filtered blood into the patient.

A thirty-fourth aspect is a method according to the thirty-second or thirty-third aspect, further comprising removing selected elements from the plasma component via a sorbent.

A thirty-fifth aspect is a method according to the thirty-second or thirty-third aspect, further comprising removing selected elements from the filtered plasma via a sorbent.

Thus, systems, devices and methods for TWO STAGE FILTRATION FOR BLOOD FLUID REMOVAL PROCESSES are described. Those skilled in the art will recognize that the preferred embodiments described herein may be altered or amended without departing from the true spirit and scope of the disclosure, as defined in the accompanying claims.

It will be understood that pumps, valves, or other components that may be employed in the field of hemodialysis, ultrafiltration, or the like, while not shown, may be used in the devices, systems and methods described herein to facilitate the removal of fluid from blood or plasma; to drive flow of blood, plasma, replacement fluid, dialysate, enrichment fluid, or the like; or the like.

In the claims that follow, the designators "first", "second", "third" and the like are used for purposes of distinguishing between elements and not for purposes of enumerating the elements or for defining a sequence of the elements. For example, a "third" outlet does not necessarily imply that there are three outlets but rather that the "third" outlet is distinct from the "first" outlet. By way of further example, a "third" outlet does not necessarily come later in time than a "first" outlet.

We claim:

1. A medical device comprising:
   a housing defining an interior, wherein the interior has a blood compartment, a plasma compartment, and a fluid compartment;
   a first filter disposed in the interior of the housing, wherein the first filter separates at least a portion of the blood compartment from at least a portion of the plasma compartment and wherein the first filter is configured to allow plasma components, but not cell components, of blood to pass through the first filter from the blood compartment to the plasma compartment;
   a second filter disposed in the interior of the housing, wherein the second filter separates at least a portion of the plasma compartment from at least a portion of the fluid compartment, and wherein the second filter is configured to allow fluid and small molecules less than 60,000 Da, but generally not larger components greater than 60,000 Da, to pass through the second filter from the plasma compartment to the fluid compartment;
   a first outlet positioned on the blood compartment to exit cell enriched fluid from the blood compartment and out of the housing; and
   an inlet in communication with the plasma compartment or the reduced fluid compartment.

2. A medical device according to claim 1, further comprising:
   an inlet in communication with the blood compartment; and
   a second outlet in communication with the fluid compartment.

3. A medical device according to claim 2, further comprising a third outlet in communication with the plasma compartment.

4. A system comprising:
   a medical device according to claim 3; and
   a sorbent medium in fluid communication with the plasma compartment of the medical device and downstream of the third outlet.

5. A system according to claim 4, further comprising a manifold having a first inlet in communication with the blood compartment of the medical device, a second inlet in communication with the plasma compartment of the medical device and downstream of the sorbent medium, and an outlet in communication with the first and second manifold inlets.

6. The system of claim 4, wherein the sorbent medium is disposed within the plasma compartment.

7. The system of claim 4, wherein the sorbent medium is disposed within the fluid compartment.

8. A medical device according to claim 1, wherein the first filter comprises a first filter porous fiber having a first lumen, and wherein at least a portion of either the blood compartment or the plasma compartment is defined by the first lumen of the first filter porous fiber.

9. A medical device according to claim 8, wherein the second filter comprises a second filter porous fiber having a second lumen, and wherein at least a portion of either the fluid compartment or the plasma compartment is defined by the second lumen of the second filter porous fiber.

10. A medical device according to claim 9, wherein a first portion of the plasma compartment is defined by the exterior of the first filter porous fiber, and wherein the device further comprises a manifold having at least one opening in communication with the first portion of the plasma compartment and the lumen of the second filter porous fiber.

11. A medical device according to claim 9, further comprising a manifold having at least one opening in communication with the lumen of the first filter porous fiber and the lumen of the second porous fiber.

12. A medical device according to claim 1, wherein either the first filter, the second filter, or both the first and the second filters, comprise a membrane.

13. A medical device according to claim 12, wherein the membrane is disposed across the housing.

14. A medical device according to claim 1, wherein the device is in the form of a cartridge.

15. The medical device of claim 1, further comprising a mixing chamber where blood from the fluid compartment is added prior to returning the blood to the patient.

16. The medical device of claim 1, further comprising a recirculating loop connecting the any one of the blood compartment, plasma compartment, and fluid compartment.

17. The medical device of claim 1, further comprising one or more conduits in fluid communication with the second outlet to divert a portion of fluid out of the housing.

18. The medical device of claim 1, further comprising one or more valves or flow restrictor to divert all or a portion of the fluid out of the housing.

19. A medical device, comprising
a housing defining an interior, wherein the interior has a blood compartment, a plasma compartment, and a fluid compartment;
a first filter disposed in the interior of the housing, wherein the first filter separates at least a portion of the blood compartment from at least a portion of the plasma compartment, and wherein the first filter is configured to allow plasma components, but not cell components, of blood to pass through the first filter from the blood compartment to the plasma compartment;
a second filter disposed in the interior of the housing, wherein the second filter separates at least a portion of the plasma compartment from at least a portion of the fluid compartment, and wherein the second filter is configured to allow fluid and small molecules less than 60,000 Da, but generally not larger components greater than 60,000 Da, to pass through the second filter from the plasma compartment to the fluid compartment;
an outlet positioned on the blood compartment to exit cell enriched fluid from the blood compartment of the housing; and
a sorbent disposed within the plasma compartment or with the reduced fluid compartment, wherein the sorbent is configured to selectively absorb one or more components from plasma or reduced plasma, respectively.

20. A method comprising:
passing a patient's blood into a medical device of claim 1 to form a plasma component and a cell component;
either dialyzing the plasma component to obtain dialyzed plasma or filtering fluid from the plasma component to obtain reduced fluid plasma; and
combining the cell component and the dialyzed plasma or the reduced fluid plasma to generate dialyzed blood.

21. A method according to claim 20, further comprising introducing the dialyzed plasma or the reduced fluid plasma into the patient.

22. A method according to claim 20, further comprising removing selected elements from the plasma component via a sorbent.

23. A method according to claim 20, further comprising removing selected elements from the dialyzed plasma or the reduced fluid plasma via a sorbent.

* * * * *